United States Patent
D'Souza

(10) Patent No.: US 7,425,543 B2
(45) Date of Patent: Sep. 16, 2008

(54) MICROENCAPSULATED MATERIALS AND METHOD OF MAKING SAME

(75) Inventor: Martin J. D'Souza, Duluth, GA (US)

(73) Assignee: The Corporation of Mercer University, Macon, GA (US)

( * ) Notice: Subject to any disclaimer, the term of this patent is extended or adjusted under 35 U.S.C. 154(b) by 393 days.

(21) Appl. No.: 10/231,791

(22) Filed: Aug. 29, 2002

(65) Prior Publication Data

US 2004/0043079 A1  Mar. 4, 2004

Related U.S. Application Data

(63) Continuation-in-part of application No. 08/434,542, filed on May 4, 1995, now Pat. No. 6,555,110, which is a continuation-in-part of application No. 07/977,057, filed on Nov. 16, 1992, now abandoned.

(51) Int. Cl.
A61K 31/7088 (2006.01)
A61K 9/50 (2006.01)

(52) U.S. Cl. .................. 514/44; 424/489; 424/491; 424/213.3; 514/885; 514/963

(58) Field of Classification Search ............ 424/489, 424/491; 427/213, 3; 514/44, 885, 963
See application file for complete search history.

(56) References Cited

U.S. PATENT DOCUMENTS

| 3,137,631 A | 6/1964 | Soloway |
| 3,429,827 A | 2/1969 | Ruus |
| 3,663,685 A | 5/1972 | Evans |
| 3,663,686 A | 5/1972 | Grotenhuis |
| 3,663,687 A | 5/1972 | Evans |
| 3,758,678 A | 9/1973 | Lindsey et al. |
| 3,937,668 A | 2/1976 | Zolle |
| 3,962,414 A | 6/1976 | Michaels |
| 4,147,767 A | 4/1979 | Yapel, Jr. |
| 4,169,804 A | 10/1979 | Yapel, Jr. |
| 4,186,183 A | 1/1980 | Steck et al. |
| 4,230,687 A | 10/1980 | Sair et al. |
| 4,349,530 A | 9/1982 | Royer |
| 4,356,259 A | 10/1982 | Banba |
| 4,671,954 A | 6/1987 | Goldberg et al. |
| 4,674,480 A | 6/1987 | Lemelson |
| 4,680,174 A | 7/1987 | Jarvis, Jr. et al. |
| 4,764,359 A | 8/1988 | Lemelson |
| 4,925,661 A | 5/1990 | Huang |
| 4,963,367 A | 10/1990 | Ecanow |
| 5,017,379 A | 5/1991 | Lemelson |
| 5,069,936 A | 12/1991 | Yen |
| 5,129,877 A | 7/1992 | Gallo et al. |
| 5,690,954 A | 11/1997 | Illum |
| 3,202,731 A1 | 9/2003 | Grevenstuk et al. |
| 2002/0177568 A1* | 11/2002 | Stinchcomb et al. ......... 514/44 |
| 2004/0043079 A1* | 3/2004 | D'Souza ................... 424/491 |
| 2005/0089576 A1* | 4/2005 | Moreau ..................... 424/486 |

FOREIGN PATENT DOCUMENTS

WO  WO 94/10980  * 5/1994

OTHER PUBLICATIONS

Hackh's Chemical Dictionary, McGraw-Hill, Inc, 1969, p. 57.*
J.H. Ratcliff et al., J Pharm. Pharmacol., 36, 431-436, 1984.
S. S. Davis et al., J Controlled Release, 4, 293-302, 1987.
Rhein, Biotech. Newswatch, Nov. 4, 1993.
Herve et al., Transplant. Proc., 1991, 23(1): 1692.

* cited by examiner

Primary Examiner—David A Saunders
(74) Attorney, Agent, or Firm—Jason A. Bernstein; Powell Goldstein LLP

(57) ABSTRACT

A method of forming microspheres of a bioactive material, such as a protein polymer or drug by nebulizing a solubilized form of a material to be encapsulated and an encapsulating material, such as albumin, in a stirred chilled solvent system comprising a vegetable oil, mineral oil and/or a lower alcohol such that the formed microspheres demonstrate intracellular bioactivity when taken up by macrophages.

24 Claims, 17 Drawing Sheets

Fig. 8: Effect of different doses of soluble (Sol.) and microencapsulated (MC) CNI-1493 on endotoxin-induced $TNF^\alpha$ levels in a whole blood model \* - Significance at $P < 0.05$ Fig. 9: Effect of different doses of soluble (Sol.) and microencapsulated (MC) CNI-1493 on endotoxin-induced IL-$\beta$ levels in a whole blood model \* - Significance at $P < 0.05$

NO FIG. 12

MICROENCAPSULATED MATERIALS AND METHOD OF MAKING SAME

CROSS-REFERENCE TO RELATED APPLICATIONS

This application is a continuation-in-part of application U.S. application Ser. No. 08/434,542, filed May 4, 1995, now U.S. Pat. No. 6,555,110, which is a continuation-in-part of application Ser. No. 07/977,057, filed Nov. 16, 1992 (now abandoned), all of which are commonly assigned to the assignee of the present application. The disclosures of all these applications are incorporated by reference in their entirety herein.

FIELD OF THE INVENTION

The present invention relates to the field of drug delivery systems. Specifically, the present invention relates to methods for preparing microencapsulated drugs using non-antigenic, biodegradable materials and also to microencapsulated compositions that are targeted to phagocytic cells such as macrophages, endothelial cells, Kupffer cells, dendritic cells and the like, or a diseased organ (such as the liver, kidneys, lungs, heart, spleen), or a diseased site (such as tumors, arthritic joints), which digest the biodegradable coating, releasing the intact drug or active component either intracellularly or at the site of accumulation. Such compositions are useful in the treatment and prevention of diseases.

BACKGROUND OF THE INVENTION

Microencapsulation of water-soluble compounds contained in albumin microspheres ("MS") has been demonstrated by our laboratory (and disclosed in previous co-pending applications) to target phagocytic cells such as macrophages/monocytes, which produce the majority of the pro-inflammatory cytokines. This technique has been demonstrated to improve the efficacy of cytokine inhibiting compounds such as neutralizing antibodies. We have further evaluated the method of preparation of albumin microspheres containing other categories of drugs such as CNI-1493 (a guanylhydrazone compound which inhibits p38 MAP kinase), clodronate (a bisphosphonate), antioxidants such as pyrrolidine dithiocarbamate, and antisense oligomers to NF-kB. Microencapsulation of these compounds has improved inhibition of cytokines such as TNF, and IL1-beta in an in-vitro whole blood model, endotoxin shock model, and a bacterial septic shock model. We also have evaluated the preparation and completed the efficacy testing of a melanoma vaccine preparation, which worked very well in preventing tumors in mice.

SUMMARY OF THE INVENTION

In a first embodiment of the present invention the various process parameters, materials and reaction conditions of the emulsification methodology previously developed (and described in the copending application(s) cited above) are expanded.

Drug delivery to specific diseased sites can aid in reducing side effects in patients, thereby preventing toxicity. By using drugs in a microencapsulated form, exposure of the drug to non-diseased organs and tissue can be prevented.

A methodology to produce microencapsulated monoclonal antibodies by the emulsification method, with the use of olive oil as the emulsification media, has been previously disclosed in the copending application(s). We disclose herein additional data after evaluating bioactive protein drugs, namely, anti-sense oligonucleotides to NF-kB, in several different oils as the emulsification media, and under different temperatures and we have also evaluated the process with the use of different aqueous solvents to dissolve the drugs.

In a second embodiment of the present invention microspheres are prepared by a novel nebulization method with different examples of drugs, different solvents, different temperatures and methodology variations.

Other classes of drugs evaluated using this emulsification method are as follows:
a) Bioactive protein drugs: (for example anti-sense oligonucleotides to NF-kB);
b) Vaccine preparation: An anti-tumor (melanoma tumor) vaccine preparation;
c) Chemical drugs: such as CNI-1493 (a guanylhydrazone compound) and clodronate (a bisphosphonate).

In this embodiment we have evaluated different solvents, different temperatures and methodology variations. The drug evaluated with this nebulization method is the anti-sense oligonucleotides to NF-kB.

In a particular embodiment, the present invention provides a method of encapsulating a bioactive material by nebulization, comprising:
a. dissolving albumin in water;
b. solubilizing antisense oligonucleotides (oligomers) to NF-kB in phosphate buffered saline (PBS);
c. mixing the dissolved albumin and the solubilized antisense oligonucleotides (oligomers) to NF-kB together;
d. cooling the mixture formed in step c.;
e. providing a solvent;
f. cooling the solvent of step e.;
g. maintaining the solvent of step f. at a cooled temperature to form a solvent system;
h. nebulizing the dissolved albumin and the solubilized antisense oligonucleotides (oligomers) to NF-kB into the solvent while the solvent of step g. is stirred;
i. evaluating the solvent system containing the microencapsulated albumin-drug microspheres of step h. for size to obtain microspheres;
j. crosslinking the microspheres with glutaraldehyde while stirring and maintaining the solvent system at a cooled temperature;
k. washing the microspheres of step j. with a solvent;
l. sizing the microspheres of step k.; and,
m. freeze drying the microspheres of step l.

The above delivery system shows that the anti-sense oligonucleotides to NF-kB can be used very effectively to inhibit cytokine-mediated processes involving phagocytic cells such as macrophages, white cells dendritic cells and endothelial cells. From these studies several other applications are relevant as follows:

A) Cytokine Related Diseases:
a) Fibrosis Syndrome: Anti-sense compounds to TGF-beta can be used to inhibit TGF-beta participation in fibrosis syndrome.
b) Rheumatoid arthritis: Anti-sense compounds to TNF-alpha and IL-1-beta can be used in rheumatoid arthritis.
c) Transplant Rejection: Anti-sense compounds to TNF-alpha and IL-1-beta can be used to suppress cytokine release (e.g., TNF-alpha and IL-1-beta) in organ transplantation.
d) Re-perfusion Injury: Anti-sense compounds to TNF-alpha and IL-1-beta can be used to suppress cytokine release in re-perfusion injury.

e) Septic Shock: Pyrrolidine dithiocarbamate (an anti-oxidant drug) can be used to suppress cytokine release (e.g., TNF-alpha and IL-1-beta). This drug inhibits NF-kB activation. NF-kB is the nuclear transcription factor which is responsible for the activation of pro-inflammatory cytokines B) Vaccine Delivery System:

a) Anti-Tumor Vaccines: The microspheres can be used as an effective vaccine delivery system for several types of vaccine preparations—similar to the melanoma tumor vaccine preparation demonstrated in this application.

b) Anti-AIDS Vaccines: The microspheres may possibly be used as an effective vaccine delivery system for anti-AIDS viruses. The AIDS virus actually infects and multiplies within the macrophages and since the microspheres are very effectively taken up into the macrophages, the addition of an anti-AIDS vaccine preparation into the microspheres could directly target the macrophages. Also these microspheres could contain anti-AIDS drugs such as AZT, which would release the drug directly at the site where the AIDS virus is known to multiply, namely within the macrophages.

C) Anti-Tumor Sustained Drug Delivery System:

a) Interleukin-12 Sustained Release Microspheres In The Treatment Of Cancer

Sustained release of therapeutic agents for the treatment of cancer is appealing considering the fact that therapy is usually long-term. It offers the possibility of using lower doses to achieve similar therapeutic effects as conventional non-sustained dosage forms. With the advent of biotechnology and the advances in the techniques of molecular biology, our antitumor arsenal has rapidly expanded to include protein drugs, peptides and cytokines. These new weapons, although potent, still need suitable delivery systems. Being protein in nature, these agents may be targets of enzymes in the blood. As a result injecting these agents requires very high doses which are not only cost prohibitive, but also potentially dangerous. Interleukin-12 is a recently discovered heterodimeric cytokine. It has been shown in various animal models of cancers to have tremendous antitumor potential. Using genetically engineered fibroblasts, it has been demonstrated that sustained presence of lower concentrations of IL-12 produce the same antitumor effects as larger concentrations that are not sustained. However, it is not easy to produce genetically engineered cells and is even more difficult to adapt it for mass therapy in general due to the considerations of cost and the amount of labor involved. Better alternatives exist in the form of particulate drug delivery systems such as microspheres that can not only shield such protein drugs from the enzymes in the blood, but can also sustain their release. Microspheres also have the added advantage of large scale production in addition to being amenable to preparation using a wide variety of biodegradable polymers.

We have evaluated the use of biodegradable albumin microspheres to sustain the release of IL-12. When administered intraperitoneally to C57BL/6 mice bearing subcutaneous melanomas, the microspheres significantly prolonged the survival when administered at half the weekly dose of the solution formulation. The microsphere dosage form also resulted in generally lower levels of liver and kidney function enzymes, suggesting lower toxicity.

D) Transfection System:

The microspheres can be used as an effective tool for transfection of genetic material into cells. Some of the current methods of cell transfection result in a significant number of cell deaths during transfection processes such as microporation. Since the microspheres used in our studies are less than 1 micron in size, they are readily taken up into the cells and can transfer the drug/material within the microspheres directly into cells.

Other features and advantages of the present invention will become apparent upon reading the following detailed description of embodiments of the invention, when taken in conjunction with the appended claims.

BRIEF DESCRIPTION OF THE DRAWINGS

The invention is illustrated in the drawings in which like reference characters or references designate the same or similar parts or parameters throughout the figures (unless otherwise noted) of which:

Figures 5, 6:
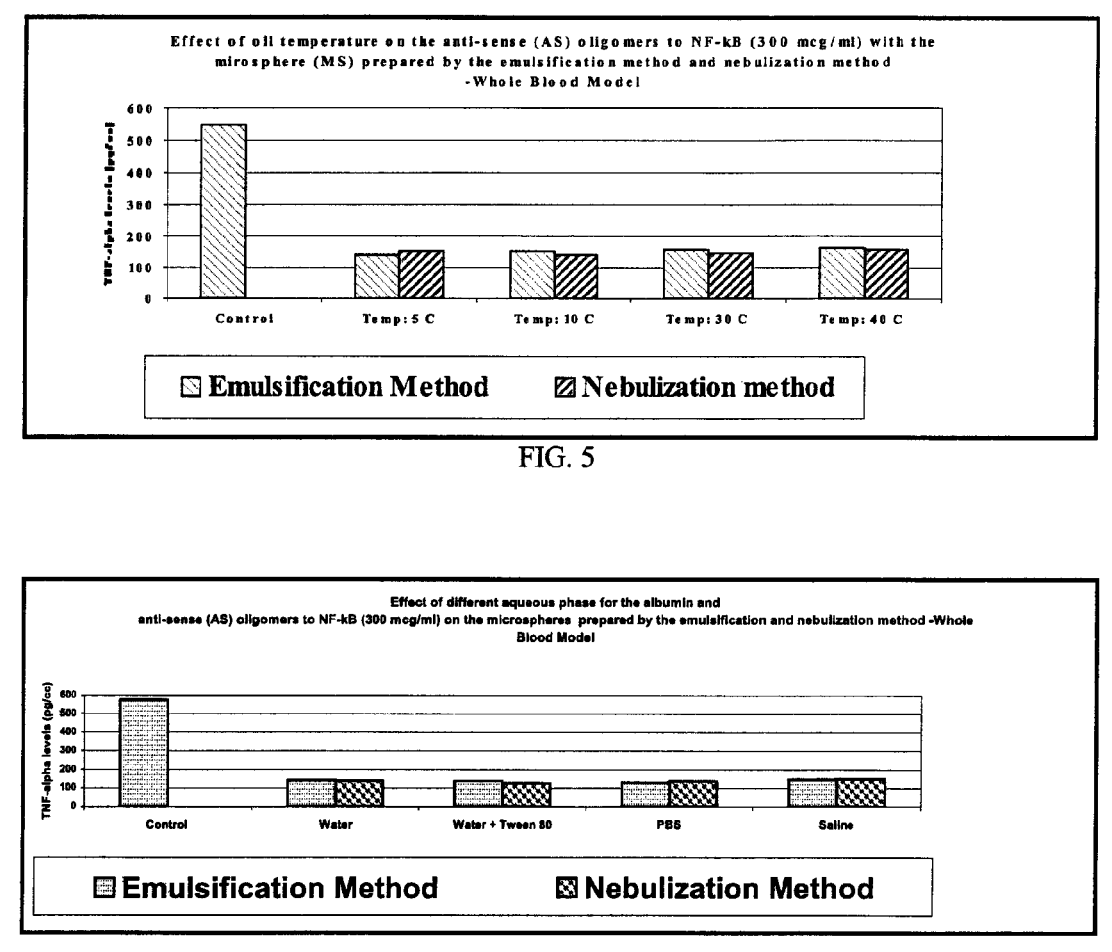

FIG. 5 shows the TNF-alpha levels with different temperatures used in the manufacturing process of the anti-sense (AS) oligomers to NF-kB by the Emulsification Method and the Nebulization Method.

FIG. 6 shows the TNF-alpha levels with different aqueous phases tested in the manufacturing process of the anti-sense (AS) oligomers to NF-kB by the Emulsification Method and the Nebulization Method.

FIG. 12 intentionally omitted.

DETAILED DESCRIPTION OF THE EMBODIMENTS

Figure 1:
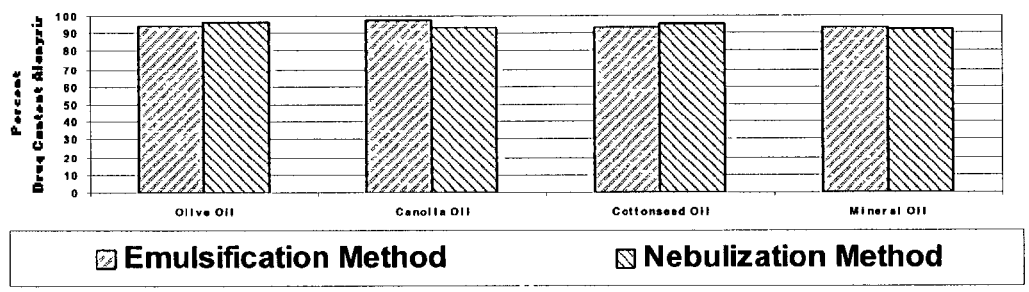
FIG. 1 shows the percent drug content analysis of the anti-sense (AS) oligomers to NF-kB by the Emulsification Method and the Nebulization Method with different oils prepared at 5 degrees C. using water as the aqueous phase for dissolution of the drug.
Figure 2:
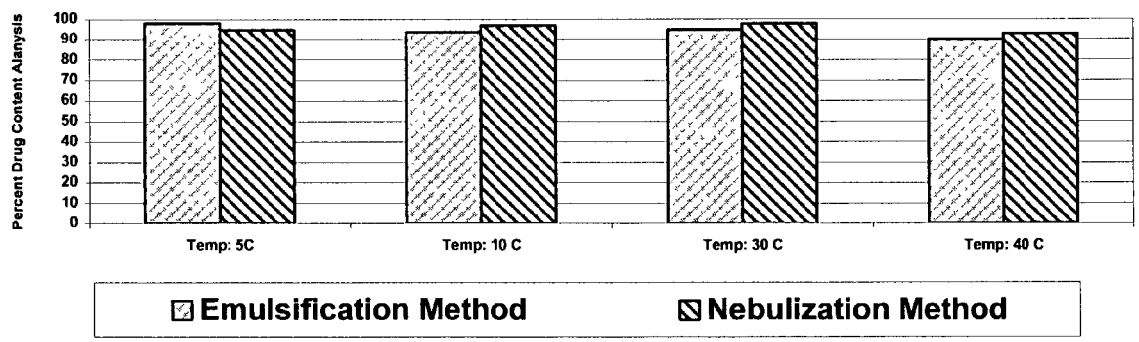
FIG. 2 shows the percent drug content analysis of the anti-sense (AS) oligomers to NF-kB by the Emulsification Method and the Nebulization Method of batches prepared at different temperature settings using water as the aqueous phase for dissolution of the drug and olive oil.
Figure 3:
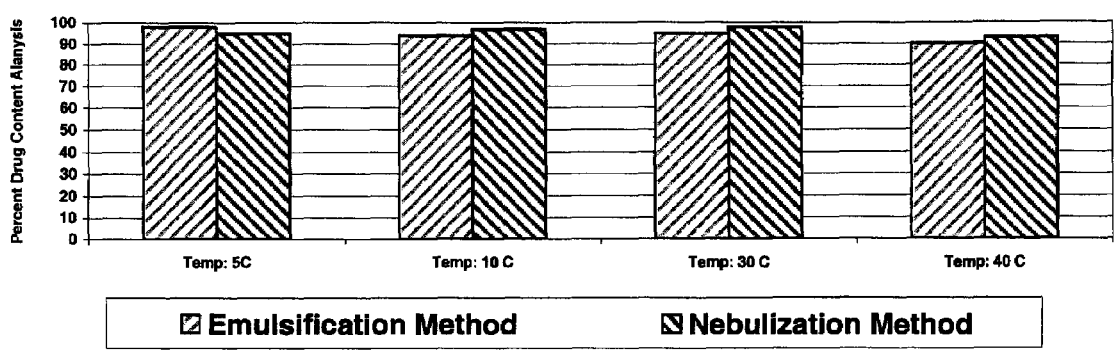
FIG. 3 shows the percent drug content analysis of the anti-sense (AS) oligomers to NF-kB by the Emulsification Method and the Nebulization Method with different aqueous phases prepared at 10 degrees C. using olive oil.
Figure 4:
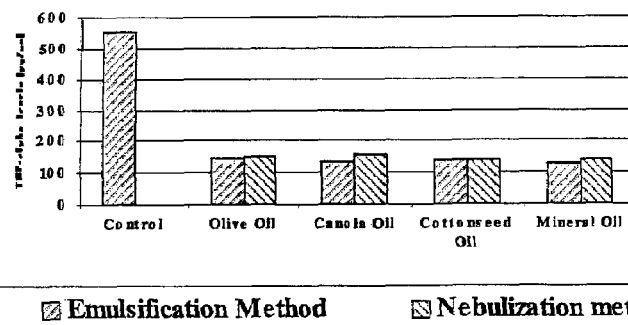
FIG. 4 shows the TNF-alpha levels using different oils to manufacture the microspheres of the anti-sense (AS) oligomers to NF-kB by the Emulsification Method and the Nebulization Method.

We will first describe the expansion of the emulsification methodology originally disclosed in prior copending application(s).

We have further expanded the testing of microspheres prepared with different drugs, oils, at different process temperatures, different aqueous solvents used to dissolve the drug and have also evaluated variations in methodology of manufacture based on the initial patent application wherein the microspheres were prepared with monoclonal antibodies to cytokine antagonists using albumin as the polymer matrix and olive oil as the emulsifying media by the emulsification methodology.

Example 1 describes encapsulation by emulsification of a representative bioactive protein, namely the anti-sense oligonucleotides to nuclear transcription factor NF-kB. Process parameter expansion included the testing of canola oil, cottonseed oil and mineral oil. The results showed that the oils tested performed well. Other bioinert vegetable and other oils, such as but not limited to, sunflower, safflower, soybean, palm, palm kernel, coconut, caster, peanut, gingley, fish, sesame, rice bran, and the like, depending on particular bioinert characteristics, and subcomponents thereof, such as, but not limited to, monounsaturated (MUFA), polyunsaturated (PUFA) and essential fatty acids (EFA), as well as mixtures of the foregoing. Other mineral oils, including, but not limited to, heavy, light and various subfractions and combinations thereof are contemplated as being within the scope of the present invention.

The temperature range of the solvent cooling was tested and broadened. Temperature range of 5-40 degrees C. was tested and found to produce acceptable results. Temperatures below about 5 degrees C. may result in at least partial freezing of aqueous components and may be undesirable.

Further, the selection of aqueous phase was expanded to now include, but not be limited to, water, phosphate buffered saline, water plus Tween® 80, and saline.

Example 2 describes the formation of microspheres of a representative tumor vaccine drug, namely, extracellular antigen, and the bioactivity obtained.

Example 3 describes the formation of microspheres of an aqueous soluble drug, namely, CNI-1493, a guanylhydrazone, and the bioactivity obtained. The test results showed that the CNI-1493 microencapsulated form using the method of the present invention was more efficacious than the corresponding doses of the soluble, non-encapsulated form in attenuating endotoxin or cytokine release.

Example 4 describes the formation of microspheres of a representative chemical drug, namely, clodronate, a bisphosphonate, and the bioactivity obtained.

Example 5 describes the formation of microspheres of a representative bioactive protein, drug, namely, anti-sense oligonucleotides to NF-kB, and the bioactivity obtained.

Example 6 describes the formation of microspheres of anti-sense oligonucleotides to NF-kB by the novel nebulizing method of the present invention, and the bioactivity obtained.

The invention will be further described in connection with the following examples, which are set forth for purposes of illustration only. Parts and percentages appearing in such examples are by weight unless otherwise stipulated. It is to be noted that unless otherwise stated the method of forming the microspheres used olive oil.

EXAMPLES

PART 1

Example 1

Bioactive Protein Drug NF-KB

Clinical Application in Septic Shock:

Formulation and Testing of Antisense Oligomers to NF-KB

A) Introduction

NF-kB is a nuclear transcription factor, which exists in the cytosol in an inactive form complexed to IkB. Endotoxin stimulates intracellular mediators, which results in phosphorylation of IkB producing translocation of NF-kB to the nucleus with subsequent activation of DNA. The mRNA for the synthesis of multiple pro-inflammatory mediators including TNF, IL1 and IL6 is rapidly produced. We have found that microencapsulated antisense oligomers (MSASO) to the p65 subunit of NF-kB inhibits TNF, IL1 and IL6 in-vitro. Anti-sense compounds have the potential to be very useful therapeutic agents by virtue of their ability to inhibit specific protein synthesis. However, a limiting factor of antisense therapy has been difficulty in obtaining adequate intracellular penetration by these large compounds. Our previous work has demonstrated improved effectiveness in cytokine inhibition using antisense to NF-kB by microencapsulated intracellular delivery. Microencapsulation provides improved delivery of the antisense compound as intracellular oligonucleotides are rapidly transported to the nucleus. Our previous studies have confirmed this hypothesis by greatly improving the effectiveness of microencapsulated antisense to the p65 moiety of NF-kB in a rat model of endotoxic shock and sepsis.

B) Preparation of the Anti-Sense Oligonucleotides to NF-kB by Albumin.

1) 50 mg of human albumin was dissolved in 2 cc of one of pyrogen free water.

2) The antisense oligonucleotides (oligomers) to NF-kB was separately solubilized in phosphate buffered saline (PBS) at a concentration of 25 mg/cc.

3) The above two solutions were mixed together for approximately 30 minutes.

4) The resulting mixture was cooled to 5 degrees C.

5) 20 cc of olive oil was taken in a 50 cc beaker and cooled to 5 degrees C. and maintained at that temperature in an ice bath.

6) The mixture of albumin and oligonucleotides was added to the oil and emulsified with the aid of a Branson Sonifier at medium setting for 20 minutes.

7) The emulsion containing the microencapsulated albumin-drug microspheres were evaluated for size with the use of a laser particle sizer until the microspheres were about 1 micron in diameter.

8) The microspheres were cross-linked with 0.5 cc of a 25% w/v solution of glutaraldehyde for 1 hour with constant stirring using a tissue homogenizer at high setting while maintaining the temperature at approximately 5 degrees C. with the aid of an ice bath.

9) The microspheres were washed with three 20 cc washes of methanol and finally sized while being suspended in the final methanol wash, with the aid of sequential HPLC filters (50, 20, 10, 5, and 1 micron size).

10) The microspheres were freeze dried and stores in a refrigerator until used.

In all cases the microspheres were suspended in pyrogen free water or saline before use.

The above procedure was repeated in order to evaluate to use of different types of oils as the emulsifying media, and different temperatures on manufacture were also evaluated in addition to the 5 degree C. described above. Finally, in addition to water, different solvents were also evaluated as the media for dissolution of the drug. The specifics of each of the parameters evaluates are as follows:

a) Effect of Different Oils:

Different oils such as canola oil, cottonseed oil and mineral oil were used for the study and was compared to olive oil used previously for the manufacture of the microspheres. It is to be understood that any bioinert vegetable or mineral oil can be used.

b) Effect of Different Temperatures:

The microspheres were prepared under wide variations of temperature such as 5, 10, 30 and 40 degrees C. The method of the present invention can thus be performed at a temperature range of from about 5-40 degrees C.

c) Effect of Different Aqueous Phase used to Dissolve the Drug:

In addition to water, and phosphate buffered saline (PBS), water containing Tween™ 80 (polyoxyethylene sorbitan monooleate, available from ICI Americas, Inc.) and saline were used to examine if differences would be significant.

Drug content analysis and efficacy studies evaluating TNF-alpha suppression was conducted using the In-vitro Whole Blood Model. The following variations in the manufacture procedure were evaluated.

C) Experimental Method:

a) Drug Content Analysis:

Drug content analysis was determined by HPLC methods developed in our laboratory.

b) Efficacy Studies evaluating TNF-alpha suppression using the in-vitro Whole Blood Model.

The preparations were evaluated for drug efficacy with the aid of the whole blood model, briefly outlined as follows:

Blood was pooled into lavender top tubes containing EDTA. The blood was separated into three 5 ml aliquots and pre-treated for 1 hour with one of the following batches of microspheres and challenged with endotoxin (100 mcg/ml). Samples were be obtained at 0 and 4 hours post endotoxin challenge to determine the TNF-alpha levels. The efficacy of the cytokine suppression due to the addition of microencapsulated oligomers to NF-kB was compared to microspheres prepared using olive oil as described in the copending patent application.

D) Results:

Effect of Different Oils on Drug Content Analysis:

FIG. 1 shows the percent drug content analysis of the anti-sense (AS) oligomers to NF-kB by the Emulsification Method and the Nebulization Method with different oils prepared at 5 degrees C. using water as the aqueous phase for dissolution of the drug. No significant differences at a $p<0.05$ was noted between the batches. Heavy (as that term is known to those skilled in the art) mineral oil was used, though it is contemplated that light mineral oil can be used, as well as other vegetable oils.

Effect of Temperature Variations on Drug Content Analysis:

FIG. 2 shows the percent drug content analysis of the anti-sense (AS) oligomers to NF-kB by the Emulsification Method and the Nebulization Method of batches prepared at different temperature settings using water as the aqueous phase for dissolution of the drug and olive oil. No significant differences at a $p<0.05$ was noted between the batches. Below a temperature of about 5 degrees C. the aqueous phase begins to freeze and reduces productivity and activity.

Effect of Different Aqueous Phases Used on Drug Content Analysis:

FIG. 3 shows the percent drug content analysis of the anti-sense (AS) oligomers to NF-kB by the Emulsification Method and the Nebulization Method (as discussed hereinbelow in greater detail in Example 6) with different aqueous phases prepared at 10 degrees C. using olive oil. No significant differences at a $p<0.05$ was noted between the batches.

Effect of Different Oils on TNF-Alpha Suppression:

FIG. 4 shows the TNF-alpha levels using different oils to manufacture the microspheres of the anti-sense (AS) oligomers to NF-kB by the Emulsification Method and the Nebulization Method. Water was used to dissolve the drug and the temperature was maintained at 5 degrees C. No significant differences at a $p<0.05$ was noted between the various batches prepared with olive oil and the other oils tested.

Effect of Temperature Variations on TNF-Alpha Suppression:

FIG. 5 shows the TNF-alpha levels with different temperatures used in the manufacturing process of the anti-sense (AS) oligomers to NF-kB by the Emulsification Method and the Nebulization Method. Olive oil was used in this process. No significant differences at a $p<0.05$ was noted between the batches prepared at different temperature settings.

Effect of Different Aqueous Phases Used on TNF-Alpha Suppression:

FIG. 6 shows the TNF-alpha levels with different aqueous phases tested in the manufacturing process of the anti-sense (AS) oligomers to NF-kB by the Emulsification Method and the Nebulization Method. Microspheres were prepared using olive oil at 10 degree C. No significant differences at a $p<0.05$ was noted between the batches prepared using different aqueous phases.

Example 2

Tumor Vaccine Drug

Tumor Protection Studies Using Microparticle as Adjuvant or Coadjuvant in a Tumor Vaccine A) Introduction The induction of an immune response is a complex and intricate process requiring an intact immune system to evaluate. Thus, a mouse tumor model was used to evaluate the microencapsulated extracellular antigen (MECA) vaccine preparation. The antigens used in the vaccine were derived from the B16 murine melanoma cells growing in culture. The C57BL/6 mouse, syngeneic to the B16 murine melanoma cells, was used. This represents a prophylactic tumor vaccine where the mice were first vaccinated to induce an anti-tumor response. The mice were then challenged to determine if an anti-tumor response was induced with the capacity to reject the establishment of the murine melanoma.

B) Preparation of Melanoma Vaccine Preparation.

The microencapsulated vaccine preparation was made according to the method described in Example 1.

C) Experimental Methods

Immunization and Tumor Protection Studies

MECA (containing 20 µg ECA in a total of 80 µg MECA) and blank MP (microparticles) were prepared by a water-in-oil emulsion cross-linking technique using glutaraldehyde as the cross linking agent. To evaluate the anti-tumor effect of 20 µg extracellular antigen in an equivalent amount of microparticles used in the first study (80 µg MECA total), 3 groups of female C57BL/6 mice (n=5), 8-12 weeks old, were vaccinated, subcutaneously. The three groups were vaccinated with 20 µg of extra-cellular antigen (ECA) contained within a total of 80 µg of microencapsulated extracellular antigen (MECA), resuspended in a total volume of 100 µl with PBS, extra-cellular antigen in solution (ECA soln) in PBS and blank microparticles (Blank MP) in PBS, respectively. The mice were boosted every week for 3 weeks for a total of 4 injections. 7 days after the last boost the mice were challenged with $7\times10^5$ live B16 melanoma cells subcutaneously at a contralateral site, as described above. The mice were then observed for 60 days for the development of tumors and tumor size and tumor incidence was recorded.

D) Results and Discussion

Figure 7:
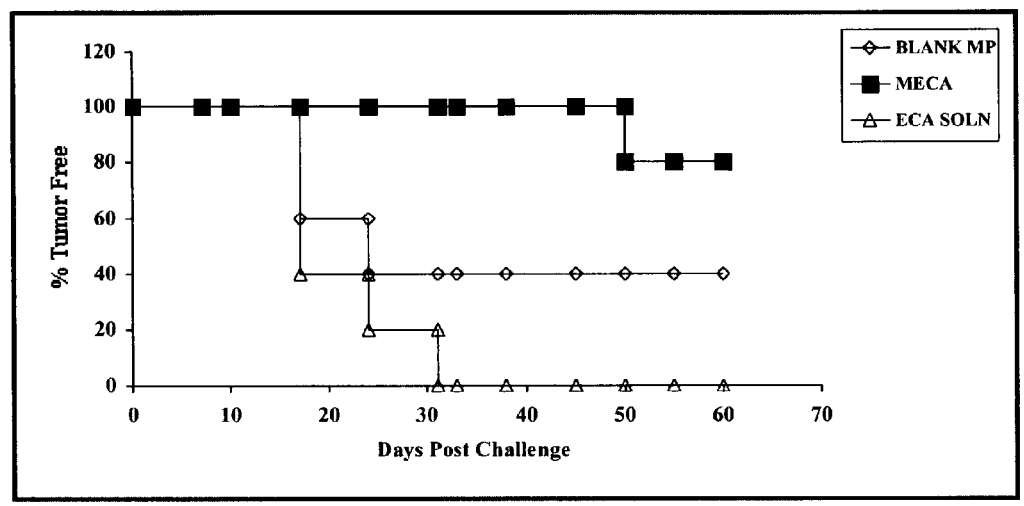
FIG. 7 shows the tumor incidence in the 20 microgram ECA contained in 80 microgram MECA study.

Female C57BL/6 mice were vaccinated with MECA (20 µg ECA contained in 80 µg total MECA), blank MP or ECA soln subcutaneously. After the first vaccination the mice were boosted once a week for three weeks. Seven days after the last vaccination boost the C57BL/6 mice were inoculated at a distant site with $7\times10^5$ live syngeneic B16 melanoma cells. The mice were subsequently monitored for the development of tumors and tumor incidence was reported (FIG. 7). The MECA group in this study remained 80% tumor free at day 60. This was in opposition to 40% tumor free in the blank microparticle group and 0% tumor free in the ECA in solution group.

The studies suggest that microencapsulating tumor antigens could have an adjuvant effect in inducing tumor immunity by targeting professional antigen presenting cells. In addition, the results of the blank microparticle group of 40% tumor free at 60 days, suggests that BSA microparticles could possibly be an excellent adjuvant for the B16 melanoma due to the homology between BSA and the B700 tumor antigen.

FIG. 7 shows the incidence in the 20 microgram ECA contained in 80 microgram MECA study. Mice were vaccinated with a total of four injections in a volume of 100 microliter PBS subcutaneously. The injections were done weekly. Seven days after the last injection the mice were challenged with $7\times10^5$ live tumor cells (B16) and tumor incidence was monitored in the MECA group, and in the controls: ECA in solution (ECA SOLN) and blank microparticles (BLANK MP).

E) Conclusion.

The in vivo dose response studies revealed that the vaccine dose of 20 µg ECA contained in 80 µg of total MECA worked very well in this study. This dose of the MECA vaccine resulted in C57BL/6 mice remaining 80% tumor free up to the 60-day study period. The studies suggest that microencapsulating tumor antigens could have an adjuvant effect in inducing tumor immunity by targeting professional antigen presenting cells. In addition, the results of the blank microparticle group of 40% tumor free at 60 days, suggests that BSA microparticles could possibly be an excellent adjuvant for the B16 melanoma due to the homology between BSA and the B700 tumor antigen.

The B16 murine melanoma tumor represents a very rigorous tumor model. For this reason it is possibly more representative of cancer in the human situations. These results do indicate that the microparticle induces a greater anti-tumor effect.

Example 3

Chemical Drug, CNI-1493: a Guanylhydrazone Compound

Application in Septic Shock

Formulation and Testing of Microencapsulated CNI-1493.

Prevention of Lethality and Suppression of Pro-Inflammatory Cytokines in Experimental Septic Shock by Microencapsulated CNI-1493

A) Introduction

Endotoxemia in animals is associated with the release of pleiotropic cytokines such as TNF-alpha and IL-1-beta from the activated macrophages and polymorphonuclear cells. Experimental drugs that inhibit the effect of these cytokines such as monoclonal neutralizing antibodies (TNF-alpha monoclonal antibody), receptor antagonists (IL-1 receptor antagonist) and receptor fusion proteins have been evaluated in animals and in the clinic for their efficacy in septic shock. Recently, a newly developed water soluble tetravalent guanylhydrazone compound termed "CNI-1493" (N,N'-bis[3,5-diacetylphenyl]decanediamide amidinohydrazone tetrahydrochloride) was shown to be efficacious in reducing lipopolysaccharide (LPS) induced TNF-alpha, IL-1-beta and IL-6 release and lethality in animals.

We have previously reported studies, which demonstrated microencapsulation of cytokine neutralizing antibodies increased their efficacy compared to the soluble form in various in vitro and in vivo disease models. Similarly, microsphere form of other cytokine antagonists may also be more efficacious than the corresponding soluble form because of the targeted uptake of the microencapsulated drugs by macrophages. In this Example, we evaluated the efficacy of microsphere form of the newly developed compound CNI-1493 by Cytokine Network Incorporated. Comparison of efficacy of the soluble and microencapsulated form of CNI-1493 was evaluated using an in vitro endotoxin-induced cytokine release whole blood model, and an in vivo model of endotoxemia and *E. Coli*-induced peritonitis.

B) Preparation of CNI-1493 Microspheres.

The microencapsulated CNI-1493 preparation was made according to Example 1.

C) Experimental Methods a) In vitro endotoxin-induced cytokine release in the whole blood model:

For each sample (n) blood was collected in EDTA (1.5 mg for each ml of blood) from five rats and pooled. After a baseline plasma sample the blood was aliquoted into five groups. There were six replicates in each group. Each group received one of the following treatments: saline or soluble form of CNI-1493—0.25, 0.5 or 1.0 microgram/ml or blank microspheres (MC) or MC form of CNI-1493—0.25, 0.5 or 1.0 microgram/ml. All groups were incubated at 37 degrees C. under an atmosphere containing 5% $CO_2$. After two hours of incubation, endotoxin (100 ng/ml) 0113 obtained from *Escherichia Coli* (Associates of Cape Cod, Wood Hole, Mass.) was added to all groups and incubated for an additional 24 hours. Plasma samples were periodically collected at 2, 4, 6 and 24 hours after endotoxin for measurement of TNF-alpha and IL-1-beta using a modified alkaline phosphatase ELISA technique.

b) In vivo model of endotoxemia: There were four rats in each group. Each group of rats received one of the following treatments i.v.: saline or soluble CNI-1493—1 mg/kg, 2 mg/kg, 5 mg/kg or 10 mg/kg or blank MC or MC form of CNI-1493—1 mg/kg, 2 mg/kg, 5 mg/kg or 10 mg/kg. All the rats were also injected with 15 mg/kg of endotoxin 0113, i.v. obtained from *Escherichia Coli* (Associates of Cape Cod, Wood Hole, Mass.) and survival was monitored for seven days. Blood was collected from the tail vein of rats at 0, 2, 4, 8, 24 and 48 hours after endotoxin for measuring TNF-alpha and IL-1-beta using ELISA.

c) In vivo model of *E. Coli*-induced peritonitis: There were six rats in each group. Each group of rats received one of the following treatments: saline, i.v. or blank MC, i.v. or soluble CNI-1493—2 mg/kg or 5 mg/kg, i.v. or MC form of CNI-1493—2 mg/kg or 5 mg/kg, i.v. or soluble CNI-1493—2 mg/kg or 5 mg/kg, i.v. plus gentamycin 15 mg/kg, i.p. or MC form of CNI-1493—2 mg/kg or 5 mg/kg, i.v. plus gentamycin 15 mg/kg, i.p. All the rats also received an injection of $1 \times 10^{10}$ CFU of live *E. Coli*, i.p., and survival was monitored for five days. Blood was collected from the tail vein of rats at 0, 2, 4, 8, 24 and 48 hours after *E. Coli* for measuring TNF-alpha and IL-1-beta levels using ELISA.

D) Results and Discussions

Figure 8:
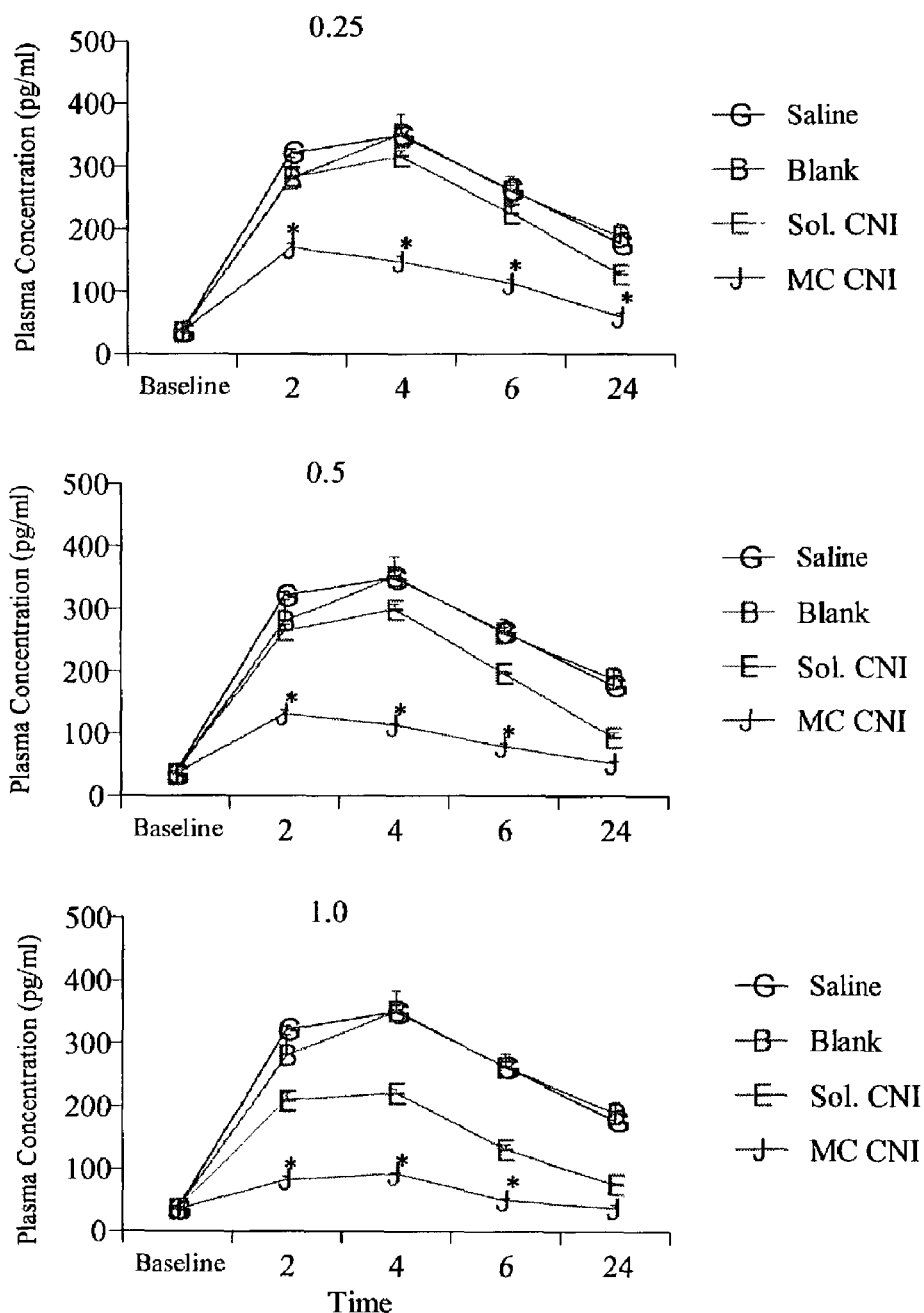
FIG. 8 shows the effect of CNI-1493 on endotoxin-induced TNF-alpha release.
Figure 9:
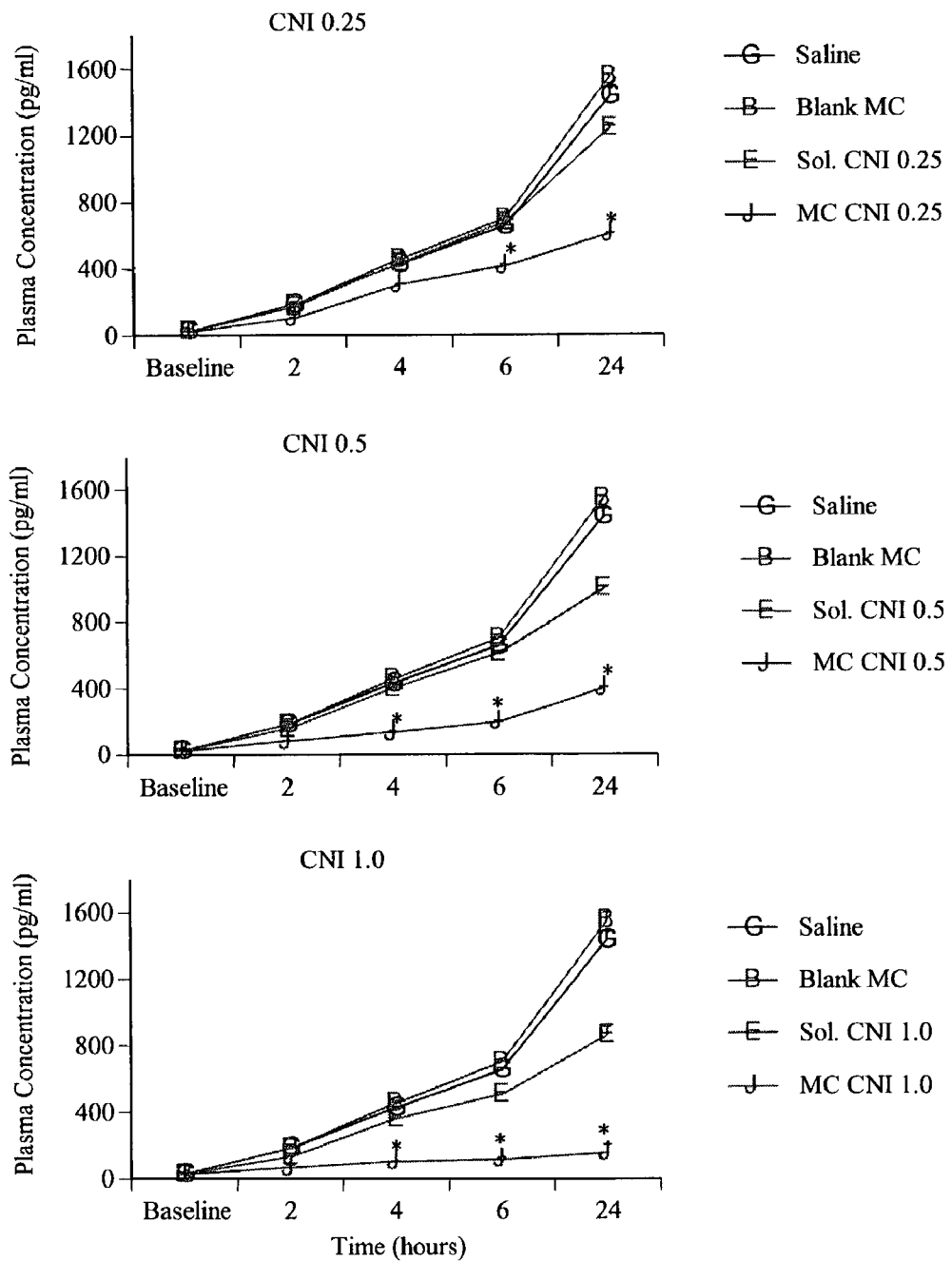
FIG. 9 shows the effect of CNI-1493 on endotoxin-induced and IL-1-beta release.

Endotoxin-induced cytokine release in whole blood model: Effect of CNI-1493 on endotoxin-induced TNF-alpha and IL-1-beta release is shown in FIGS. 8 and 9, respectively. Presence of blank MC did not significantly affect endotoxin-induced TNF-alpha and IL-1-beta release. A dose of 0.25 microgram/ml of soluble form of CNI-1493 did not alter endotoxin-induced TNF-alpha and IL-1-beta release but, 0.5 and 1.0 microgram/ml of CNI-1493 significantly attenuated endotoxin-induced TNF-alpha and IL-1-beta release. On the other hand, all doses of MC form of CNI-1493 containing 0.25, 0.5, and 1.0 microgram of CNI-1493/ml significantly (p<0.05) attenuated endotoxin-induced TNF-alpha and IL-1-beta release. In addition, the attenuation of endotoxin-induced cytokine release by all doses MC form was significantly greater than the corresponding soluble form of CNI-1493.

In vivo model of endotoxemia: The survival data is shown in Table 1.

TABLE 1

Comparison of survival rates with soluble (Sol.) and microencapsulated (MC) CNI-1493 in lethal endotoxemia.

| Treatments | Percent Survival | | |
|---|---|---|---|
| | 0 hours | 48 hours | 120 hours |
| Endotoxin alone | 100 | 0 | 0 |
| Endotoxin + 1 mg/kg Sol. CNI-1493 | 100 | 0 | 0 |
| Endotoxin + ≦1 mg/kg MC form CNI-1493 | 100 | 25 | 25 |
| Endotoxin + 2 mg/kg Sol. CNI-1493 | 100 | 0 | 0 |
| Endotoxin + ≦2 mg/kg MC form CNI-1493 | 100 | 100* | 100* |
| Endotoxin + 5 mg/kg Sol. CNI-1493 | 100 | 0 | 0 |
| Endotoxin + ≦5 mg/kg MC form CNI-1493 | 100 | 100* | 100* |
| Endotoxin + 10 mg/kg Sol. CNI-1493 | 100 | 50 | 50 |
| Endotoxin + ≦10 mg/kg MC form CNI-1493 | 100 | 100* | 100 |

*Significance at p < 0.05 when compared to equivalent doses of Sol. CNI-1493 or endotoxin alone using Mann-Whitney test.

Figure 10:
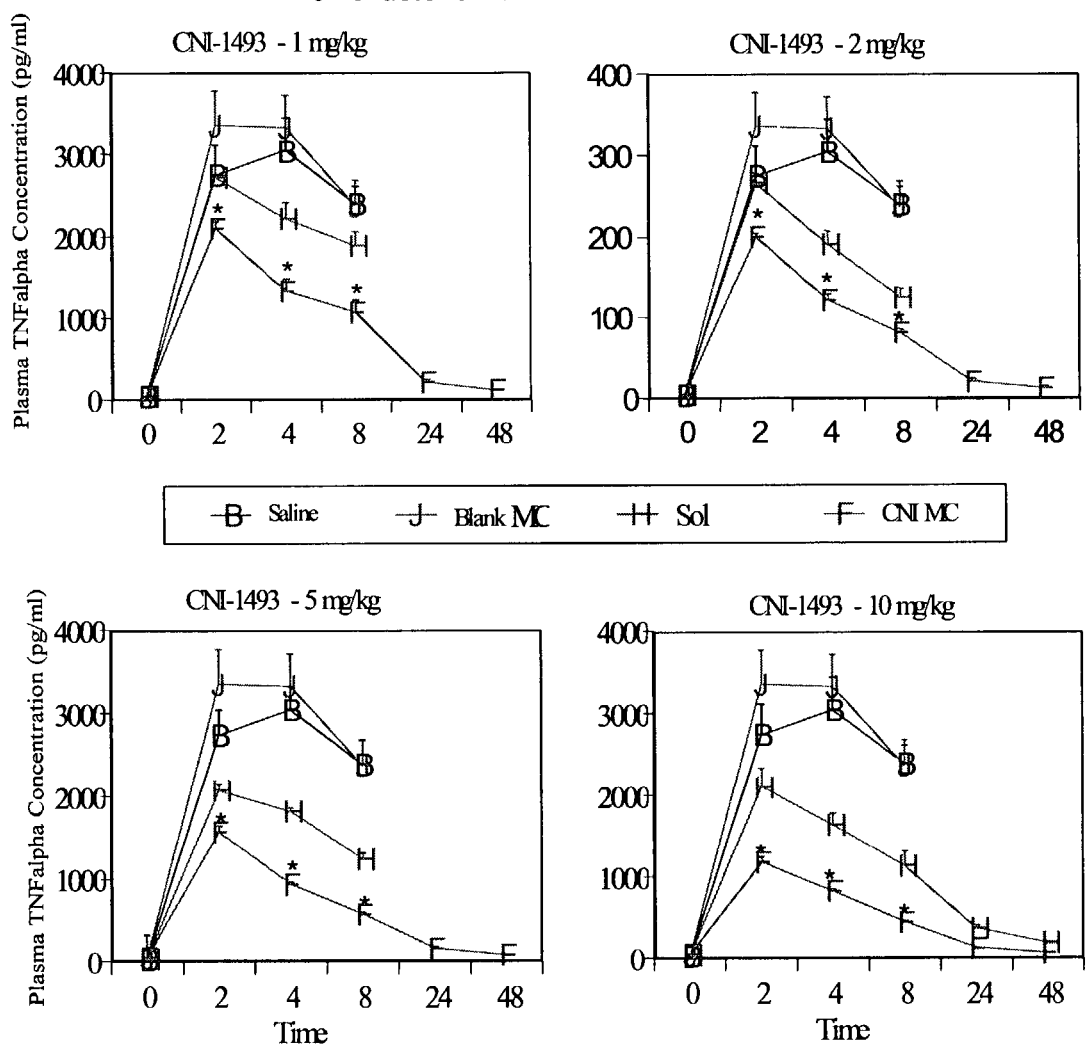
FIG. 10 shows the effect of different doses of soluble (SOL) and microencapsulated (MC) CNI-1493 on endotoxemia-induced TNF-alpha levels.
Figure 11:
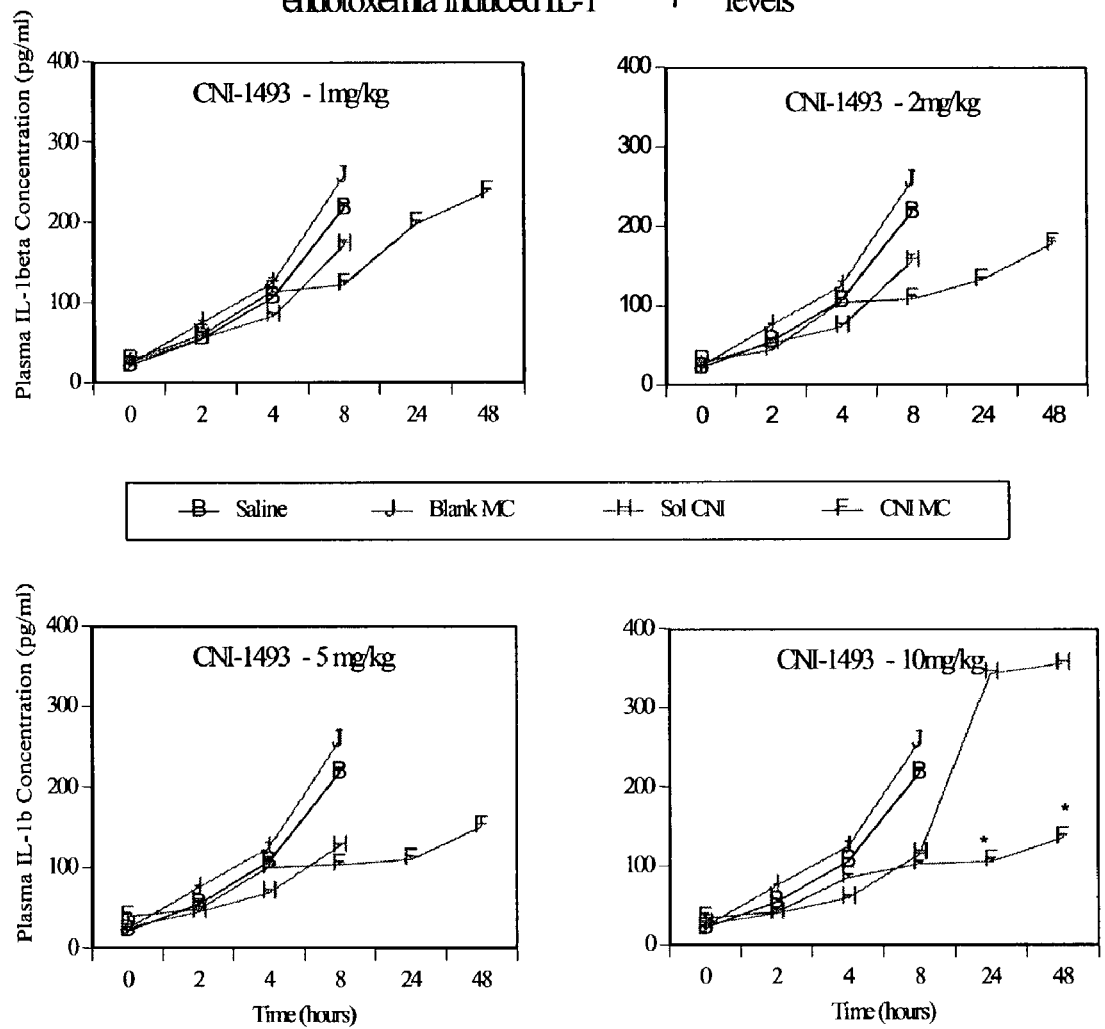
FIG. 11 shows the effect of different doses of soluble (SOL) and microencapsulated (MC) CNI-1493 on endotoxemia-induced IL-1-beta levels.

All the animals that received 1, 2, 5 mg/kg of soluble form of CNI-1493 died within 24 hours of endotoxin while 50% of the animals that received 10 mg/kg of soluble form of CNI-1493 and 25% of the animals in the group that received 1 mg/kg dose of MC form of CNI-1493 survived for seven days after endotoxin. On the other hand, all the animals (100%) in the group that received 2, 5, and 10 mg/kg of the MC form of CNI-1493 survived for seven days after endotoxin. The cytokine levels for this study are shown in FIG. 10 and FIG. 11 (FIG. 12 intentionally omitted). Soluble and MC form of CNI-1493 lowered endotoxemia-induced TNF-alpha levels to a greater extent and IL-1-beta levels to a smaller extent. However, MC form of CNI-1493 was significantly better than the soluble form of CNI-1493 in attenuating both TNF-alpha and IL-1-beta levels.

*E. Coli*-induced peritonitis model of septic shock: The survival data is shown in Table 2.

TABLE 2

Comparison of survival rates with soluble (Sol.) and microencapsulated (MC) CNI-1493 in *E. Coli*-induced peritonitis.

| Treatments | Percent Survival | | |
|---|---|---|---|
| | 0 hours | 48 hours | 168 hours |
| *E. Coli* + saline | 100 | 0 | 0 |
| *E. Coli* + blank microspheres | 100 | 0 | 0 |
| *E. Coli* + 2 mg/kg Sol CNI-1493 | 100 | 0 | 0 |
| *E. Coli* + 2 mg/kg MC form CNI-1493 | 100 | 0 | 0 |
| *E. Coli* + 2 mg/kg Sol. CNI-1493 + gentamycin | 100 | 50% (3 in 6)* | 17% (1 in 6) |
| *E. Coli* + 2 mg/kg MC form CNI-1493 + gentamycin | 100 | 67% (4 in 6)* | 67% (4 in 6)* |
| *E. Coli* + 5 mg/kg Sol. CNI-1493 | 100 | 0 | 0 |
| *E. Coli* + 5 mg/kg MC form CNI-1493 | 100 | 17% (1 in 6) | 17% (1 in 6) |
| *E. Coli* + 5 mg/kg Sol. CNI-1493 + gentamycin | 100 | 67% (4 in 6)* | 50% (3 in 6) |
| E. Coli + 5 mg/kg MC form CNI-1493 + gentamycin | 100 | 83% (5 in 6)* | 83% (5 in 6)* |

*Significance at p < 0.05 when compared to *E. Coli* + saline group or *E. Coli* + blank microspheres group using Mann-Whitney test.

All the animals that received saline or blank MC or 2 mg/kg of soluble form of CNI-1493 or 5 mg/kg of soluble CNI-1493 or 2 mg/kg of MC form of CNI-1493 pretreatment died within 4 to 8 hours of *E. Coli* administration. There was minimal protection against lethality with a 17% survival rate after treatment with either 5 mg/kg of MC form of CNI-1493 or a 2 mg/kg of a soluble form of CNI-1493 and gentamycin. Administration of gentamycin also increased the survival rate to 50% in the group that received 5 mg/kg of soluble form of CNI-1493 pretreatment, 67% in the group that received 2 mg/kg MC form of CNI-1493 and to 83% in the group that received 5 mg/kg MC form of CNI-1493. Both soluble and MC form of CNI-1493 lowered *E. Coli*-induced TNF-alpha and IL-1-beta levels and the MC form of CNI-1493 was significantly better than the soluble form of CNI-1493 in attenuating *E. Coli*-induced TNF-alpha and IL-1-beta levels.

Microencapsulation of CNI-1493 improved effectiveness in both the in vitro and in vivo models. The results show that MC form of CNI-1493 was more efficacious than the corresponding doses of soluble form of CNI-1493 in attenuating endotoxin or *E. Coli* induced cytokine release and lethality. In previous studies using microencapsulated cytokine neutralizing antibodies, we saw an improvement in efficacy in inhibition of endotoxin-induced cytokine release and prevention of lethality due to endotoxin or *E. Coli*-induced peritonitis compared to the corresponding soluble form of the neutralizing antibodies. It may be that the effectiveness of microencapsulated compounds (excluding the sustained release form) is magnified by the intracellular release in phagocytic cells. CNI-1493 released from the microspheres after being phagocytozed by phagocytic cells provides a higher intracellular concentration that leads to effective suppression of the proinflammatory cytokines by an intracellular mechanism of action. Previous studies have shown that soluble CNI-1493 can suppress LPS induced cytokines such as TNF-alpha, IL-1-beta and IL-6 from peripheral blood monocytes as seen in this study. The mechanism by which CNI-1493 inhibits TNF-alpha synthesis is speculated to be at the translational or post-translational level. In this study MC form of CNI-1493 strongly inhibited endotoxin-induced TNF-alpha and IL-1-beta levels while the soluble form of CNI-1493 inhibited endotoxin-induced TNF-alpha and IL-1-beta levels to a smaller extent both in the in vitro and in vivo models. The extent of endotoxin-induced TNF-alpha inhibition by the lowest dose of MC form of CNI-1493 (0.25 microM) was similar to that produced by the highest dose of soluble form of CNI-1493 (1.0 microM) in the in vitro whole model. This indicates that theoretically the MC form of CNI-1493 could be at least four times as potent as the soluble form of CNI-1493 in inhibiting endotoxin-induced TNF-alpha synthesis.

MC form of CNI-1493 (2 mg/kg) provided complete protection against lethal endotoxemia while there was no survival with the same dose of soluble form of CNI-1493 (2 mg/kg) or a only 50% survival with five times higher dose of the soluble form of CNI-1493 (10 mg/kg). Complete protection by the MC form of CNI-1493 against lethality due to endotoxemia suggests a greater effectiveness of the microencapsulated delivery system. At a dose of 5 mg/kg of CNI-1493, the survival rate in *E. Coli*-induced peritonitis model was also much higher with the combination of gentamycin and MC form of CNI-1493 (83%) compared to the combination of gentamycin and soluble form of CNI-1493 (50%). In this infectious model of lethality both soluble and MC form did not prevent lethality except when gentamycin was used in conjunction with CNI-1493. This indicates that antibiotic treatment is essential in a severe infectious state. The experimental model of peritonitis has proven to be resistant to treatment with antibiotics alone or soluble form of TNF-alpha neutralizing antibodies alone. In fact, there has been no previously reported studies that demonstrate improved survival in this model after treatment with the soluble form of cytokine antagonists except when treated with a combination of antibiotics and microencapsulated cytokine antagonists.

In conclusion, we have demonstrated the superior effectiveness of microencapsulated CNI-1493 in suppressing endotoxin-induced TNF-alpha and IL-1-beta release using an in vitro whole blood model. This improved effectiveness has produced significantly better survival in both endotoxemia and *E. Coli* peritonitis model of septic shock.

Example 4

Chemical Drud-Clodronate

Application-Glomerulonephritis

Macrophage Depletion by Albumin Microencapsulated Clodronate: Attenuation of Cytokine Release in Macrophage Dependent Glomerulonephritis A) Introduciton The macrophage plays an important role in the inflammatory process through the release of cytokines, chemokines and other substances. The role of macrophage in various inflammation-mediated disease states can be evaluated by depletion of macrophages with clodronate, a water soluble compound. Clodronate, a bisphosphonate, is a potent inhibitor of osteoclast-mediated bone reabsorption and clinically used to treat metabolic bone diseases. Clodronate in free (solution) form has little effect on macrophage function following systemic administration. However, liposomes containing clodronate are readily phagocytozed by macrophages and cause depletion of macrophages in the liver, spleen, lymph nodes and peritoneal cavity, and monocytes in the systemic circulation. We have developed a method of microencapsulation of clodronate using albumin that has several advantages over the use of liposomes. Albumin can be used as the biocompatible polymer matrix to form microspheres (MS) of varying size which has greater stability and ease of preparation when compared to liposomes. Albumin is a biodegradable, non-toxic substance that has a high efficiency of encapsulation. The purpose of this investigation is to determine if albumin MS containing clodronate: 1) will produce systemic macrophage depletion, 2) have an effect on TNF-alpha and IL-1-beta release induced by endotoxin in vitro, and 3) have an effect on macrophage infiltration in experimental glomerulonephritis (GN) in rats. The results indicate that clodronate MS effectively depleted macrophages, attenuated endotoxin-induced TNF-alpha and IL-1-beta release, and blocked experimental GN induced macrophage infiltration into the glomerulus.

B) Preparation of Microspheres.

The microencapsulated clodronate was made according to Example 1.

C) Experimental Methods a) Comparison of In Vitro Efficacy of Free Form and Microsphere Form of Clodronate in Rat Whole Blood Model: Blood from six to seven Fisher rats (F-344) weighing 200-250 grams (obtained from Harlan Sprague-Dawley) was collected via cardiac puncture and pooled for each 'n'. Ten microliter of 15% EDTA solution was added for each ml of blood to prevent clotting. The blood was aliquoted and to each ml, 25, 50 and 100 μg of free clodronate in saline or 50, 100 and 200 μg of clodronate MS (equivalent to 25, 50 and 100 μg of free clodronate respectively, since the albumin:clodronate ratio in the microencapsulated clodronate formulation was 1:1) was added. An aliquot of blood from each rat was also treated with 50 µl of saline or 400 µg of blank MS. Two hours later 100 ng/ml of endotoxin was added and the blood samples were incubated for 24 hours in an atmosphere of 5% $CO_2$ at 37 degrees C. Plasma samples were collected at baseline, 2, 4, 6 and 24 hours by centrifugation at 1000×g for 10 minutes, for measurement of TNF-alpha and IL-1-beta using a modified alkaline phosphatase ELISA procedure developed in our laboratory.

b) Macrophage Depletion by Clodronate in Healthy Rats and Rats with Anti-GBM GN: Anti-GBM globulin was raised in sheep by repeated immunization with a membrane fraction of rat kidney in Freud's Complete Adjuvant (FCA, Sigma Chemical Co., St. Louis, Mo. USA). The sheep serum was heat de-complemented and absorbed twice against rat red blood cells (10% by volume). A globulin fraction was prepared by precipitation with ammonium sulfate at a final concentration of 50% and was extensively dialyzed against phosphate buffered saline. GN was initiated by intravenous injection of sheep anti-rat GBM globulin at a dose of 100 µg/gm body weight to male Sprague-Dawley rats weighing 100-150 grams, obtained from Central Animal Services (Monash University, Clayton, Victoria, Australia). Forty-eight hours prior to initiation of anti-GBM GN, one group of rat received 5 mg of clodronate MS (assumed to contain not more than 50% clodronate by weight) and the other group received no clodronate treatment. A group of healthy normal rats that did not receive any anti-GBM GN was used as controls. Seventy-two hours after anti-GBM injection all the rats (including the healthy control rats) were sacrificed, and tissue samples of the spleen, liver and kidney were obtained. The tissue samples were then fixed in periodate lysine paraformaldehyde for four hours, washed in 7% sucrose solution and then frozen in liquid nitrogen cooled isopentane. The frozen tissue was sliced into 4 mm sections in a cryostat. Tissue sections were stained using a three layer immunoperoxidase technique. A mouse monoclonal antibody against rat ED1, a pan-macrophage marker that reacts with the cytoplasmic antigen was the primary antibody added. This was followed by a second layer of rabbit anti-mouse IgG globulin at a concentration of 1 in 100 (Dako, Glostrup, Denmark). This was followed by a peroxidase conjugated mouse immunoglobulin (Dako, Glostrup, Denmark) at a concentration of 1:100. Sections were then incubated with diamino benzadine (Sigma Chemical Company, St. Louis, Mo.), and counter stained with Harris haemotoxylin. The number of macrophages in the spleen was measured by counting ED1 positive cells in 10×1 $mm^2$ red pulp areas and averaged as cells/$mm^2$. The number of Kupffer cells in the liver was measured by counting ED1 positive cells in 10×1 $mm^2$ liver cord areas and averaged as cells/$mm^2$. Macrophages in circulation were calculated as percentage of the circulating leukocytes.

D) Results and Discussion

Our study demonstrated that small doses of clodronate encapsulated in albumin are effective in depleting ED1 positive macrophages from the liver, spleen, kidney and peripheral blood in rats. Clodronate MS also produced a prompt reduction in endotoxin stimulated TNF-alpha and IL-1-beta release which was significantly greater than clodronate in free (solution) form and prevented macrophage infiltration into the glomerulus that accumulate during experimental anti-GBM GN in rat.

Macrophage depletion has been proven to be a valuable tool in evaluating the contribution of the macrophage to the development of pathological conditions. Clodronate, a bisphosphonate has little effect on the viability of the macrophage in the free form, but encapsulated into liposomes or MS (as in this study) there was a transient depletion of the macrophage population within 24-48 hours. The depletion of macrophages by clodronate liposomes was shown to be caused by apoptosis-induced cell death. We speculate a similar mechanism of action for clodronate MS.

The reduction in endotoxin-induced TNF-alpha and IL-1-beta release after pretreatment with clodronate MS as seen in this study has also been shown by others using clodronate liposomes. It has also been shown that clodronate liposomes can attenuate cytokine gene expression in mice. In the whole blood model, we also demonstrated a greater reduction of endotoxin-induced cytokine release with clodronate MS when compared to clodronate in free form. There was nearly a complete inhibition of both TNF-alpha and IL-1-beta release at the highest dose of clodronate MS that contained, not greater than 100 µg of free clodronate. The mechanism of action of clodronate MS is likely due to phagocytosis of the albumin MS containing clodronate in a similar fashion to liposomes followed by the release of the clodronate intracellularly that produces an inhibition of cytokine release due to death of macrophages. Inhibition of cytokine release by clodronate may be beneficial in the treatment of disease states characterized by proinflammatory cytokine release.

Previous studies have shown that macrophages have an important role in induction and progression of renal damage in GN. One of the hallmarks of GN is proteinuria and macrophage infiltration. The reduction in macrophage infiltration by clodronate MS in experimental GN has been previously shown by our group. We have shown that the anti-GBM induced GN causes macrophage infiltration (8.2 cells/glomerular cross-section) and treatment with clodronate MS prevented macrophage infiltration (2.2 cells/glomerular cross-section) similar to that seen in this study. In addition, we have also shown that anti-GBM GN-induced proteinuria (43 mg/24 hr) can also be significantly reduced with clodronate MS (8.4 mg/24 hr) to the same level found in normal healthy rats (5.3 mg/24 hr). Clodronate MS may be therapeutically beneficial by depleting macrophages in GN.

Figure 13:
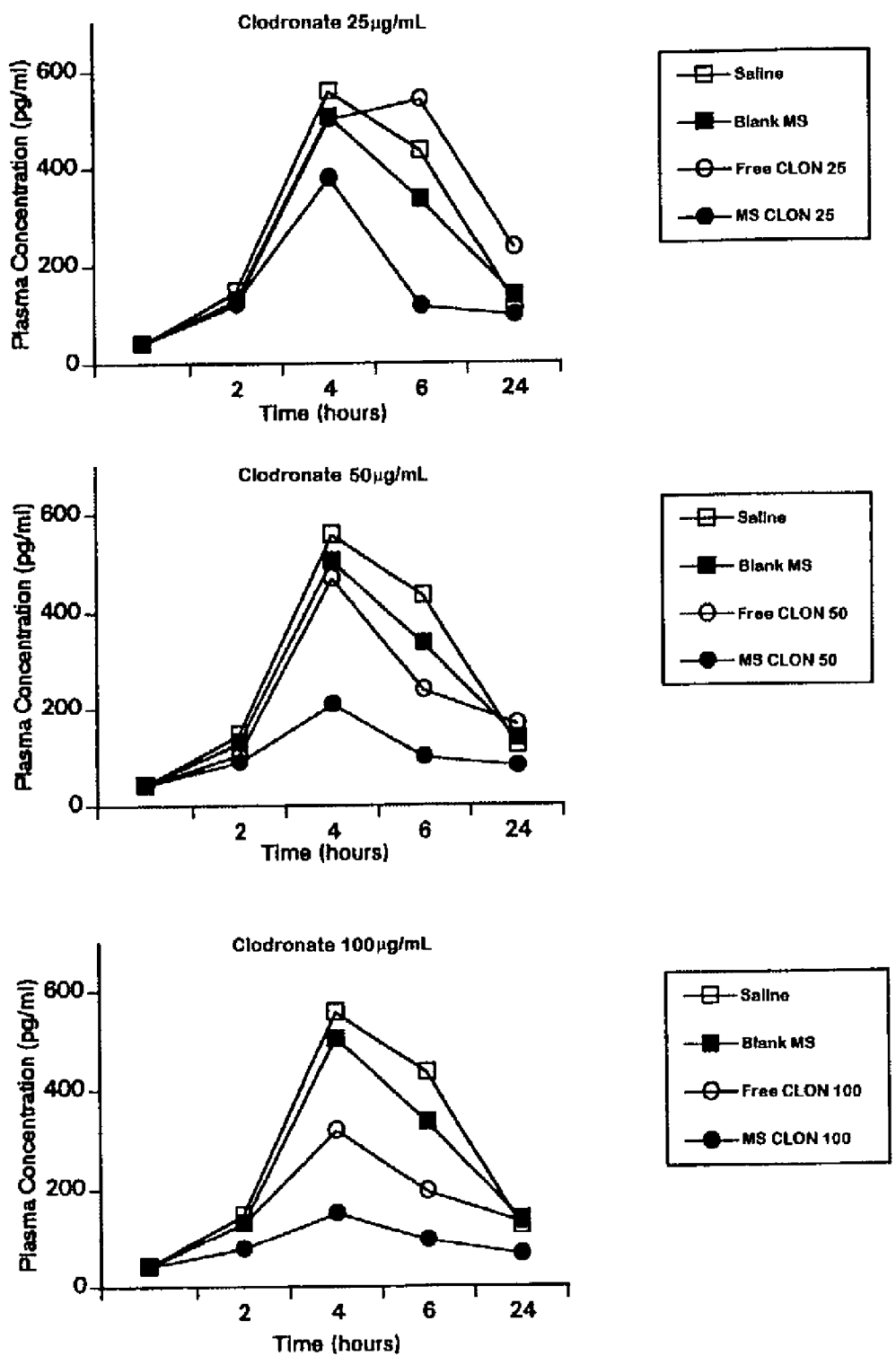
FIG. 13 shows the effect of clodronate on endotoxin-induced TNF-alpha release.
Figure 14:
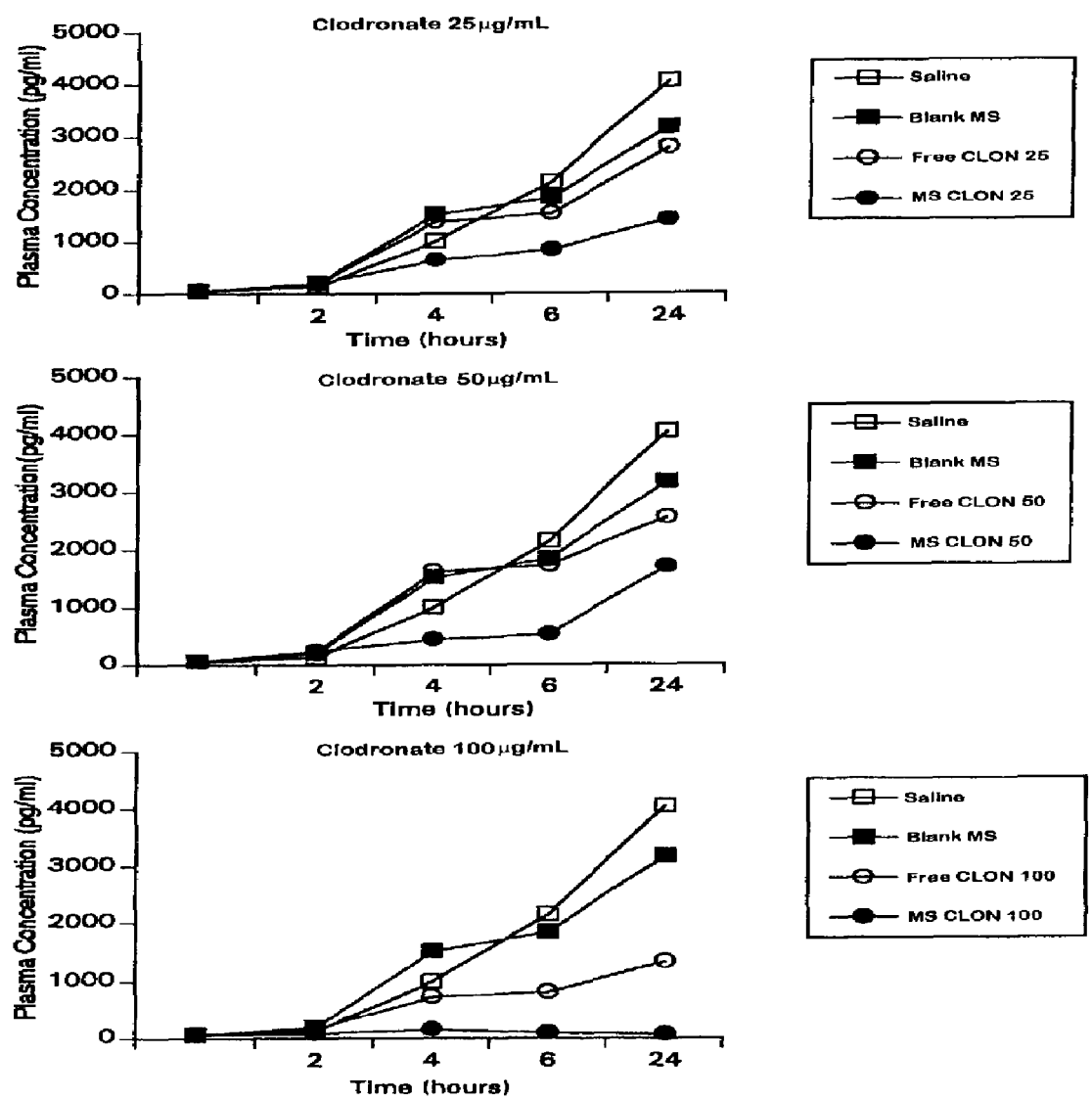
FIG. 14 shows the effect of clodronate on endotoxin-induced IL-1-beta release.

Effect of clodronate on endotoxin-induced TNF-alpha and IL-1-beta release is shown in FIGS. 13 and 14, respectively. Presence of blank MS did not significantly affect endotoxin-induced TNF-alpha and IL-1-beta release. Low (25 µg/ml) and medium (50 µg/ml) dose of free clodronate did not alter endotoxin-induced TNF-alpha and IL-1-beta release but, higher dose (100 µg/ml) of free clodronate showed a trend for attenuating endotoxin-induced TNF-alpha and IL-1-beta release. On the other hand, all doses of clodronate MS containing 25, 50, and 100 µg of equivalent free clodronate/ml significantly ($p<0.05$) attenuated endotoxin-induced TNF-alpha and IL-1-beta release.

Tissue sections stained for ED1 positive macrophages demonstrate that was a significant ($p<0.001$) reduction of ED1 positive macrophages from liver and spleen of rats that received clodronate MS compared to healthy control rats (see Table 3).

TABLE 3

Effect of clodronate MS on macrophage depletion in rats with anti-GBM GN.

| Tissue | ED1 Positive Macrophages | |
|---|---|---|
| | Untreated Controls | Clodronate MS |
| Spleen | 280 ± 23 cells/mm | 13 ± 12 cell/mm* |
| Liver | 38 ± 2.5 cells/mm | 1.8 cells/mm* |
| Blood | 13.5 ± 1.5%[a] | 1.2 ± 0.1%[a]* |

[a]Percentage of the total leucocytes;
*Statistical significance at $p < 0.001$.

There was also a significant reduction in circulating monocytes in peripheral blood (Table 3, $p<0.001$). Similarly, kidney sections stained for ED1 positive macrophages show that there was no macrophage infiltration into the glomerulus of normal healthy kidneys and induction of anti-GBM GN caused ED1 positive macrophage infiltration. Pretreatment with clodronate MS significantly reduced the macrophage infiltration in anti-GBM GN.

In conclusion, these studies demonstrate that albumin MS containing clodronate is an effective tool for total body depletion of macrophages in the rat. Depletion of macrophages by clodronate MS produced attenuation of pro-inflammatory cytokines and amelioration of experimental anti-glomerular basement membrane GN that has been demonstrated to be macrophage-dependent. Transient depletion of macrophages may be a treatment modality for macrophage-dependent disease state.

FIG. 13 shows the effect of free form of clodronate (CLON) and microsphere (MS) of CLON on endotoxin induced TNF-alpha levels in the rat whole blood model.

To each ml of blood 25, 50 and 100 μg of free clodronate in saline or 50, 100 and 200 μg of clodronate MS (equivalent to 25, 50 and 100 μg of free clodronate respectively) in saline was added. In all groups, the saline group received 50 μl of saline and blank MS group received 400 μg of blank MS for each ml of blood. Two hour later 100 ng/ml of endotoxin was added and the blood was incubated for 24 hours in an atmosphere of 5% $CO_2$ at 37 degrees C. Plasma levels after endotoxin challenge is shown in this figure. The MS form of CLON attenuated endotoxin-induced TNF-alpha levels significantly better than the free form of CLON at $p<0.05$ level.

FIG. 14 shows the effect of free form of clodronate (CLON) and microsphere (MS) of CLON on endotoxin induced IL-1-beta levels in the rat whole blood model. To each ml of blood 25, 50 and 100 μg of free clodronate in saline or 50, 100 and 200 μg of clodronate MS (equivalent to 25, 50 and 100 μg of free clodronate respectively) in saline was added. In all groups, the saline group received 50 μl of saline and blank MS group received 400 μg of blank MS for each ml of blood. Two hour later 100 ng/ml of endotoxin was added and the blood was incubated for 24 hours in an atmosphere of 5% $CO_2$ at 37° C. Plasma levels after endotoxin challenge is shown in this figure. The MS form of CLON attenuated endotoxin-induced IL-1-beta levels significantly better than the free form of CLON at $p<0.05$ level.

Example 5

Bioactive Protein Drug NF-KB

Application-Septic Shock

Method of Preparation-Emulsification Method

Preparation of Microspheres Containing Cytokine Antagonist Namely Anti-Sense Oligomers to NF-KB (Bio-Active Protein Drug)

Evaluation in Whole Blood Model, Endotoxic Shock Model and Peritonitis Model

Microencapsulated Antisense Oligomers to NF-Kb; a New Approach to Pro-Inflammatory Cytokine Inhibition A) Introduction Inhibition of individual protein synthesis is possible by antisense oligonucleotides after binding with its specific mRNA. However, inadequate intracellular penetration of antisense compounds has limited their effectiveness. Antisense compounds contained within microencapsulated albumin takes advantage of the normal phagocytic function of macrophages to deliver antisense oligonucleotides intracellularly for improved exposure of the oligomers to nuclear and cytosolic mRNA. Flourescein labeled oligonucleotides when microinjected into macrophages appears in the nucleus within minutes, thus interacting immediately with synthesized mRNA.

Studies done in our laboratory have demonstrated that albumin microcapsules 1) are rapidly phagocytozed by macrophages in-vitro and in-vivo 2) are distributed to over 90% of monocytes/macrophages in the liver, spleen, kidney and blood and 3) migrate to the area of infection. In previous studies, we have demonstrated improved efficacy of micro encapsulated neutralizing antibodies to TNF and IL1 in both in-vitro cytokine suppression and animal survival using an in-vivo fatal endotoxic shock model and a peritonitis model of infection. Thus, microencapsulated drug delivery directly targeting the macrophage, which secretes the majority of proinflammatory cytokines, may improve the efficiency of these compounds.

NF-kB has recently been described and is thought to be the nuclear transcription factor responsible for the synthesis of proinflammatory cytokines such as TNF and IL1. Other substances involved in the inflammatory process are also regulated by NF-kB. Increased activity of NF-kB has been described in sepsis and in other inflammatory conditions such as glomerulonephritis, acute respiratory distress syndrome, and inflammatory bowel disease. Thus, antisense oligonucleotides to NF-kB may alter the inflammatory response by suppressing the synthesis of the proinflammatory cytokines. Microencapsulation of these compounds may further improve efficiency by direct macrophage targeting.

The aims of the present study are as follows:

a) to determine if albumin microencapsulation of antisense oligomers to NF-kB will improve suppression of TNF, IL1, IL6 and IL8 to endotoxin stimulation in an in-vitro whole blood model and b) to determine if microencapsulated oligomers to NF-kB will suppress proinflammatory cytokines and improve survival using in-vivo endotoxic shock and peritonitis models.

B) Preparation of Microspheres.

The microencapsulated anti-sense oligonucleotides to NF-kB were made according to Example 1.

C) Experimental Methods a) In Vitro Whole Blood Model:

Samples of blood were drawn from normal human volunteers and separated into multiple 1 ml aliquots. 100 ug of E.

Coli endotoxin was added to each specimen. Cytokine levels were determined by ELISA in duplicate in each group after the following incubation times: TNF—4 hours, IL1—24 hrs.

The following groups were studied:
1. control: endotoxin+saline
2. NF-kB antisense in solution, 200 and 300 ug/ml given 1 hr prior to the addition of endotoxin
3. NF-kB non-sense (scrambled) 200 and 300 ug/ml
4. Microencapsulated antisense oligomers to NF-kB 200 and 300 ug/ml
5. Microencapsulated non-sense (scrambled) oligomers 200 and 300 ug/ml b) In Vivo Endotoxic Shock Model Endotoxic shock was produced in Fischer rats weighing approximately 150 grams by intravenous injection of 15 mg/kg of *E. Coli* endotoxin. TNF was measured by ELISA at 0, 4 hrs, 8 hrs, 24 hrs and 48 hrs. Survival was observed for 5 days (120 hrs).

After a dose response study was performed, 300 ug of microencapsulated antisense oligomers to NF-kB was injected into 10 rats and 300 ug of oligomer in solution were given intravenously to 10 rats.

c) In Vivo Peritonitis Model

Peritonitis was induced in rats by the intraperitoneal injection of $10^{10}$ organisms of *E. Coli*. gentamycin 15 mg/kg was given intraperitoneally for 3 consecutive days. TNF was measured at 0 hrs, 4 hrs, 8 hrs, 24 hrs, and 48 hrs. Survival was observed for 5 days (120 hrs).

1. Simultaneous treatment: *E. Coli* peritoneal injection and the following treatments were given simultaneously and then daily for an additional 2 days.
   a. control
   b. microencapsulated NF-kB I.V. 400 ug/rat n=10
   c. microencapsulated NF-kB I.V. 200 ug/rat n=10
   d. solution NF-kB I.V. 400 ug/rat n=10
   e. solution NF-kB I.V. 200 ug/rat n=10
2. Delayed treatment: Treatment with the above doses of oligomer initially given 4 hrs after the dose of intra peritoneal *E. Coli* (at the peak TNF level) and then for an additional 2 days.

D) Results and Discussions:

Microencapsulation of antisense oligomers to NF-kB improves pro-inflammatory cytokine inhibition by increased intracellular penetration into the macrophage. Microencapsulated antisense oligomers to NF-kB inhibit TNF>IL1>IL6>IL8 to a greater extent than equivalent amounts of oligomer in solution (p<0.05) using the in-vitro whole blood model. Microencapsulated NF-kB oligomers produced a dose dependent improvement in TNF inhibition in the endotoxic shock model in rats. 80% survival at a dose of 300 ug per rat was observed compared to 20% in the endotoxic shock model with an equivalent dose in solution (p<0.05). Microencapsulated oligomers produced 80% survival in the peritonitis model and 70% survival in the delayed treatment group compared to 30 and 20% in the solution group respectively. TNF and IL1 were inhibited to a greater extent in the microencapsulated group. Survival occurred in the delayed treatment group with microencapsulated oligomers even when given after the peak in TNF occurred.

In summary, microencapsulated oligomers to NF-kB improve pro-inflammatory cytokine inhibition both in-vitro and in-vivo with improved mortality in otherwise fatal models of endotoxic shock and peritonitis. Microencapsulated oligomers to NF-kB may be of value in the treatment of pathological conditions characterized by pro-inflammatory cytokine activation.

Figure 15:
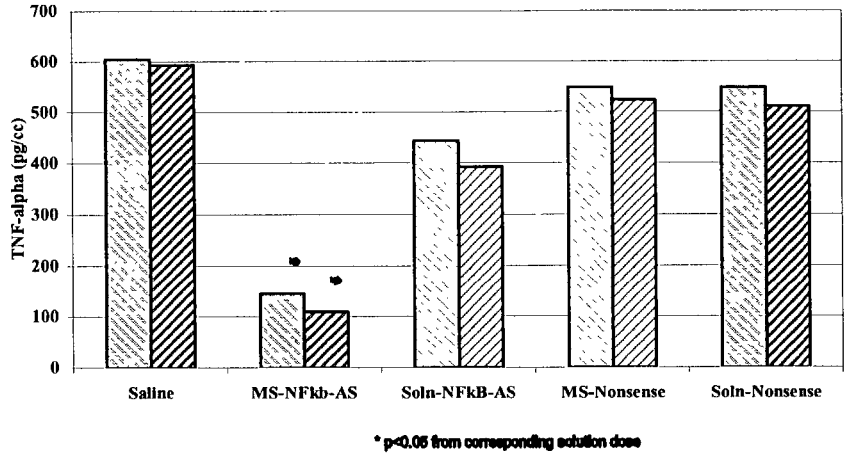
FIG. 15 shows the effect of anti-sense (AS) oligomers to NF-kB on TNF-alpha inhibition in the microsphere (MS) and solution (Soln.) formulation.

E) Results:

FIG. 15 shows the effect of anti-sense (AS) oligomers to NF-kB on TNF-alpha inhibition in the microsphere (MS) and solution (Soln.) formulation.

Figure 16:
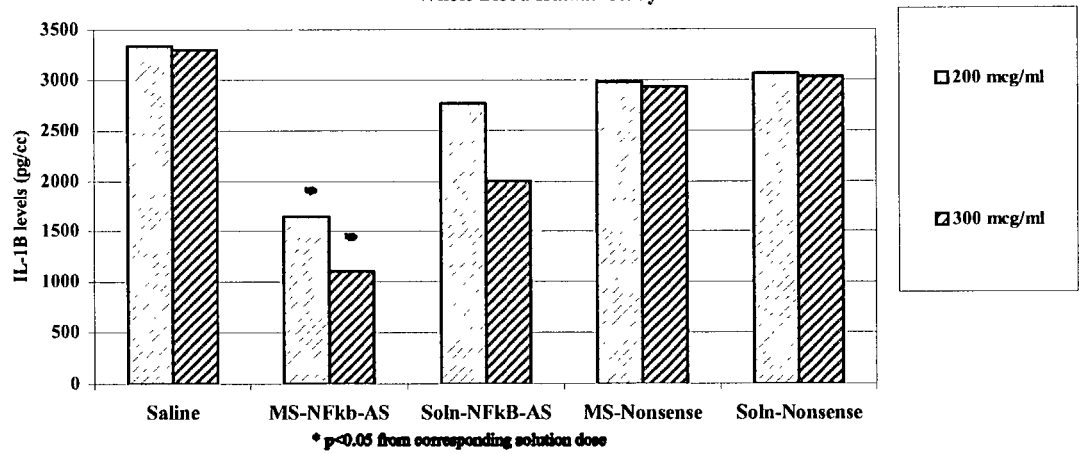
FIG. 16 shows the effect of anti-sense (AS) oligomers to NF-kB on IL-1-beta levels in the microsphere (MS) and solution (Soln.) formulation.
Figure 17:
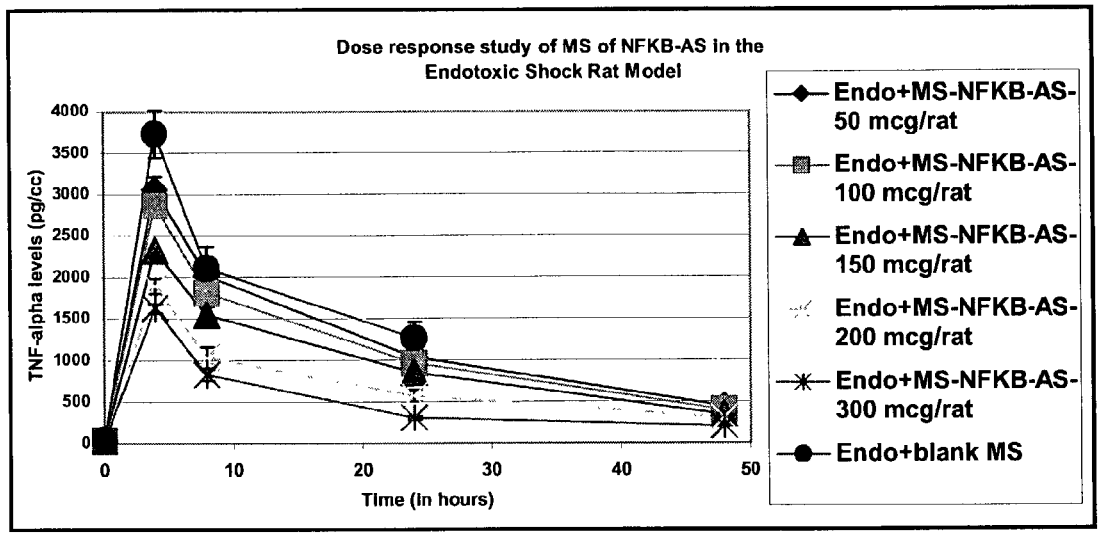
FIG. 17 shows the effect of a dose response study of microspheres of anti-sense NF-kB in the Endotoxic Shock Rat Model.

FIG. 16 shows the effect of anti-sense (AS) oligomers to NF-kB on IL-1-beta levels in the microsphere (MS) and solution (Soln.) formulation in the Whole Blood Human Study:

FIG. 17 shows the dose response study of microspheres of anti-sense NF-kB in the Endotoxic Shock Rat Model.

Figure 18:
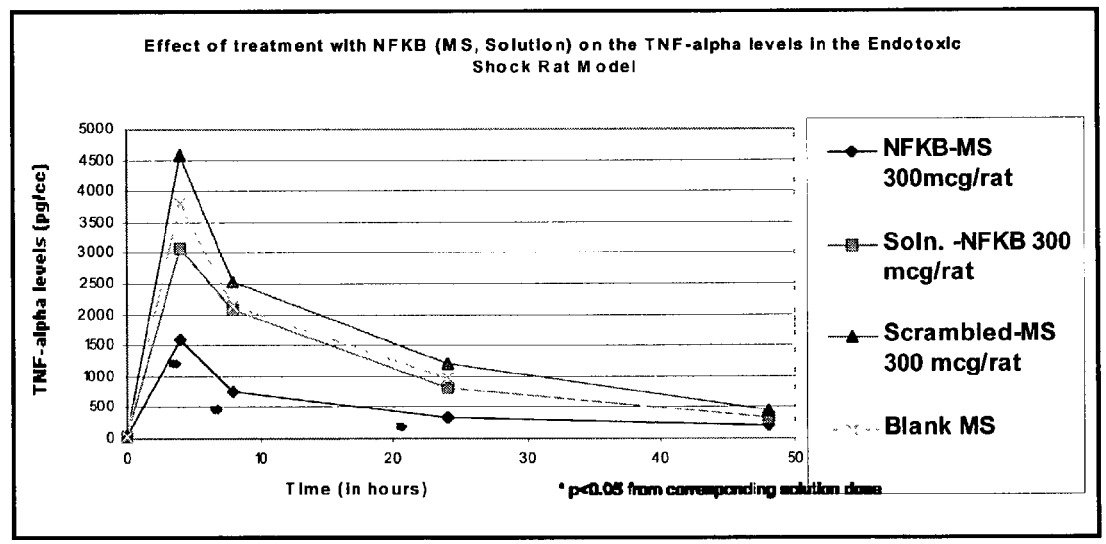
FIG. 18 shows the effect of treatment with NF-kB (microspheres and solution) on the TNF-alpha levels in the Endotoxic Shock Rat Model.

FIG. 18 shows the effect of treatment with NF-kB (microspheres and solution) on the TNF-alpha levels in the Endotoxic Shock Rat Model.

Figure 19:
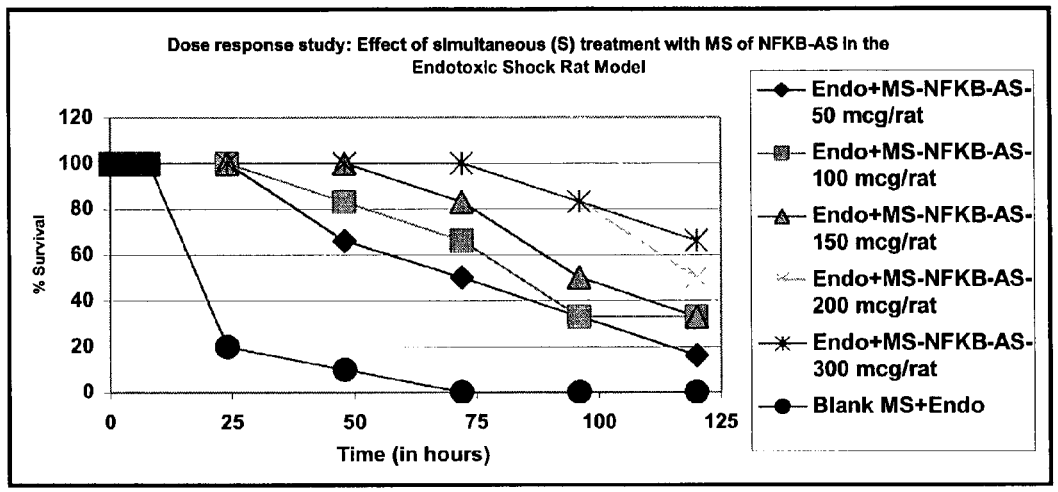
FIG. 19 shows the effect of a dose response study of simultaneous treatment with microspheres of anti-sense NF-kB on the survival in the Endotoxic Shock Rat Model.

FIG. 19 shows the dose response study of simultaneous treatment with microspheres of anti-sense NF-kB on the survival in the Endotoxic Shock Rat Model.

Figure 20:
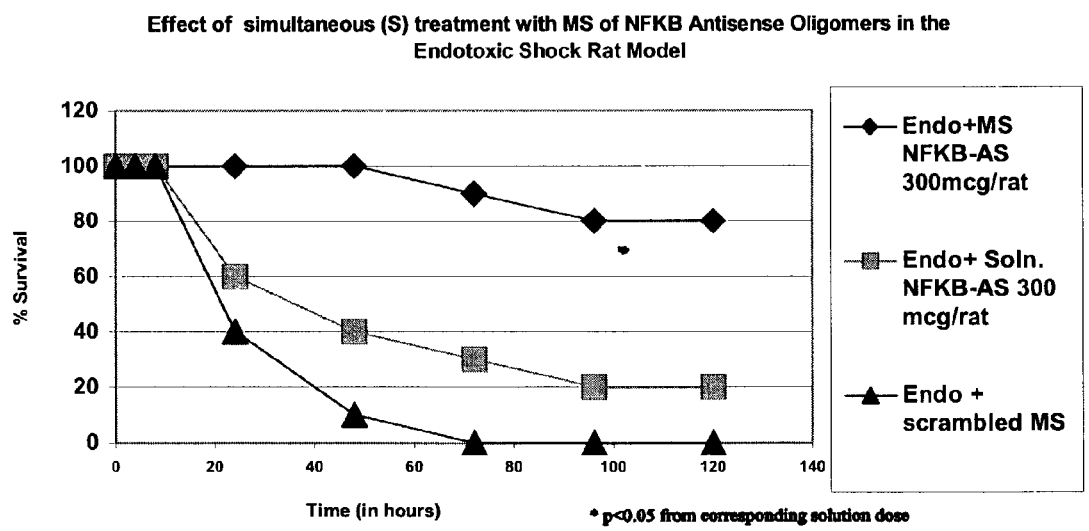
FIG. 20 shows the effect of simultaneous (S) treatment with microspheres and the solution form of anti-sense oligomers to NF-kB on the survival in the Endotoxic Shock Rat Model.

FIG. 20 shows the effect of simultaneous (S) treatment with microspheres and the solution form of anti-sense oligomers to NF-kB on the survival in the Endotoxic Shock Rat Model.

Figure 21:
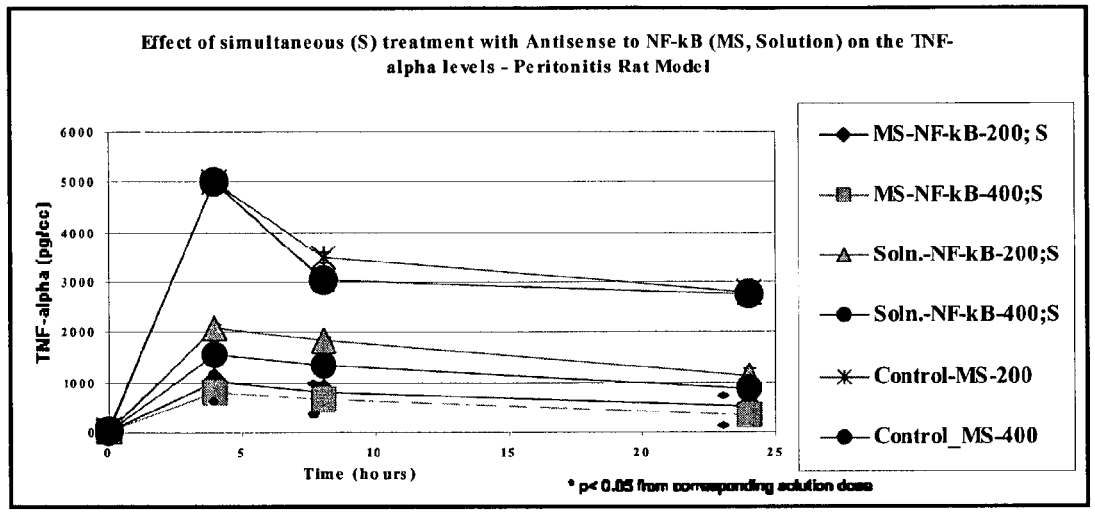
FIG. 21 shows the effect of simultaneous (S) treatment with anti-sense oligomers to NF-kB (microsphere and solution form) on the TNF-alpha levels.

FIG. 21 shows the effect of simultaneous (S) treatment with anti-sense oligomers to NF-kB (microsphere and solution form) on the TNF-alpha levels in the Peritonitis Rat Model.

Figure 22:
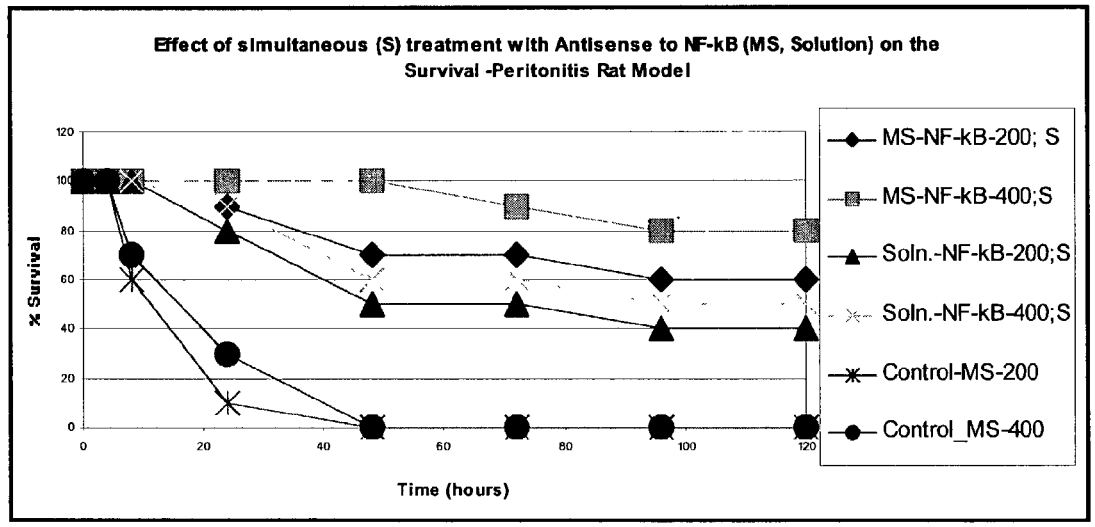
FIG. 22 shows the effect of simultaneous (S) treatment with anti-sense oligomers to NF-kB (microsphere and solution form) on survival.

FIG. 22 shows the effect of simultaneous (S) treatment with anti-sense oligomers to NF-kB (microsphere and solution form) on survival in the Peritonitis Rat Model.

Figure 23:
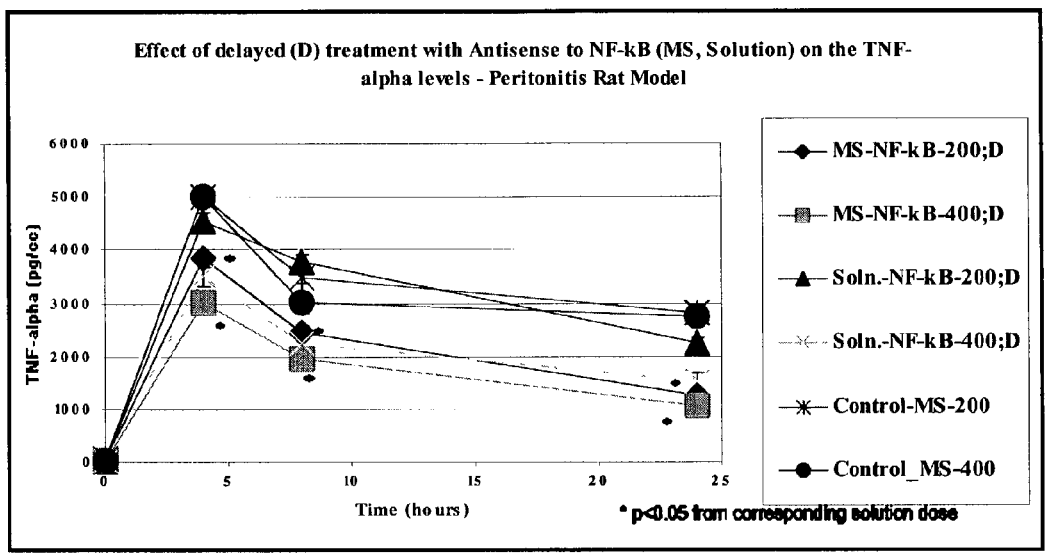
FIG. 23 shows the effect of delayed (D) treatment with anti-sense oligomers to NF-kB (microsphere and solution form) on the TNF-alpha levels.

FIG. 23 shows the effect of delayed (D) treatment with anti-sense oligomers to NF-kB (microsphere and solution form) on the TNF-alpha levels in the Peritonitis Rat Model.

Figure 24:
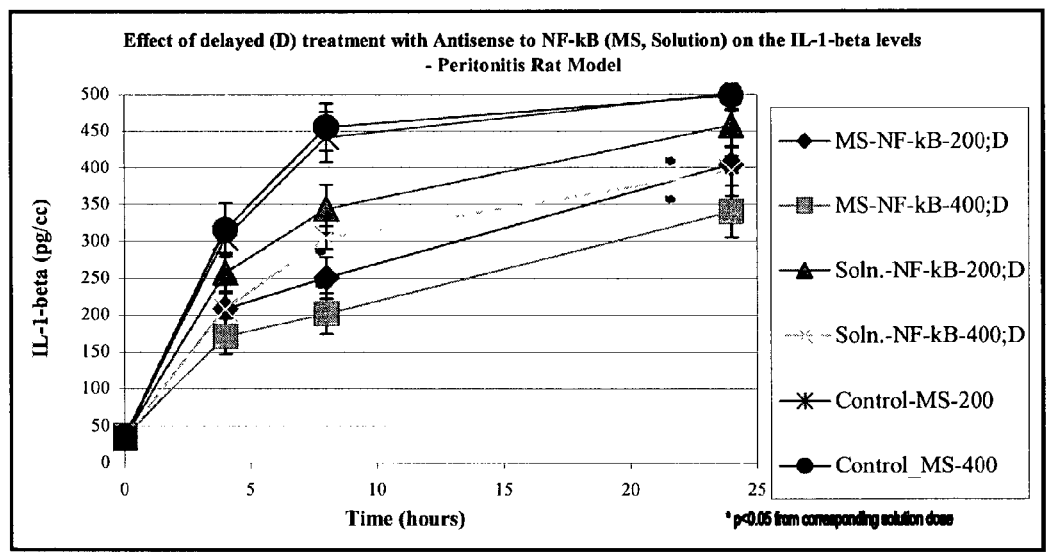
FIG. 24 shows the effect of delayed (D) treatment with anti-sense oligomers to NF-kB (microsphere and solution form) on the IL-1-beta levels.

FIG. 24 shows the effect of delayed (D) treatment with anti-sense oligomers to NF-kB (microsphere and solution form) on the IL-1-beta levels in the Peritonitis Rat Model.

Figure 25:
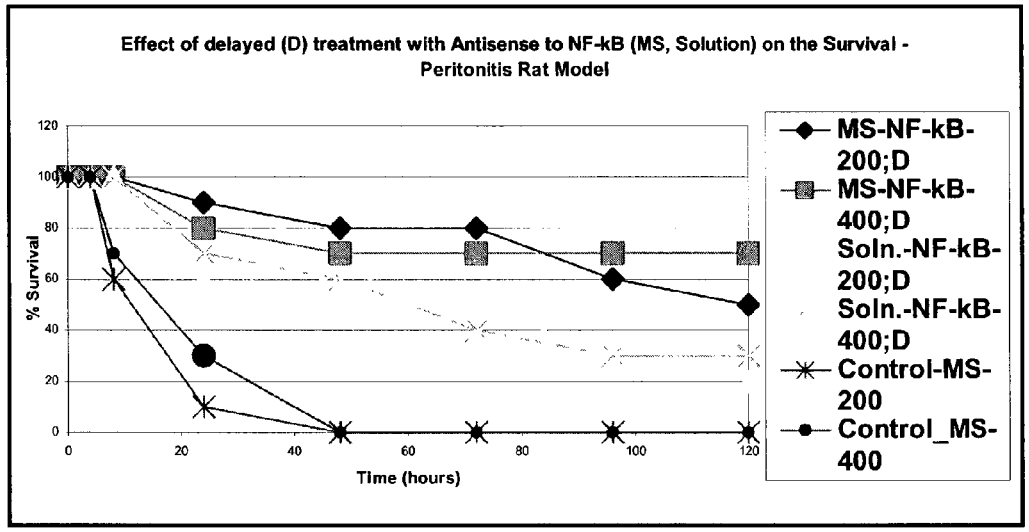
FIG. 25 shows the effect of delayed (D) treatment with anti-sense oligomers to NF-kB (microsphere and solution form) on the survival.

FIG. 25 shows the effect of delayed (D) treatment with anti-sense oligomers to NF-kB (microsphere and solution form) on the survival in the Peritonitis Rat Model.

EXAMPLES

PART 2

Evaluation of Microspheres Prepared by the Nebulization Method with Different Examples of Drugs, Different Solvents, Different Temperatures and Methodology Variations.

Figure 26:
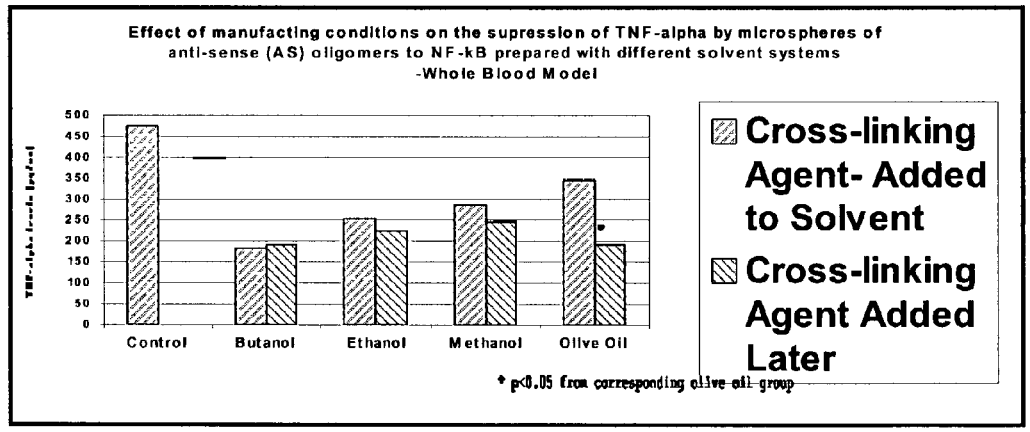
FIG. 26 shows the effect of manufacturing conditions on the suppression of TNF-alpha by microspheres of anti-sense (AS) oligomers to NF-kB prepared with different solvent systems in the Whole Blood Model.

A) Introduction:

We were interested in evaluating microspheres prepared by a nebulization method of different categories of drug types (bio-active proteins, oligonucleotides, chemicals, vaccines) and also to study the effect of variations in oils, temperature and methodologies on the preparation of microspheres. We used a biodegradable non-antigenic albumin matrix to microencapsulate the cytokine antagonists [such as anti-sense oligomers to NF-kB].

B) Experimental Methodology

Microsphere Preparation:

Nebulization Method:

General Methodology:

The general basis of this invention involves the following steps:

An aqueous solution of the drug (which may be a bioactive protein, drug or a synthetic drug) to be microencapsulated is prepared along with the encapsulating polymer (such as, but not limited to, albumin, chitosan, globulin or some other bio-degradable natural or synthetic polymer). The polymer-drug solution is then aerosolized (with the aid of some spray forming device, such as, but not limited to, an ultrasonic nebulizer) to form a fine mist-like spray. This mist or spray containing the polymer-drug (or other material) solution is then directed into a solvent system such as butanol or other lower carbon alcohol, such as, but not limited to methanol, ethanol, propanol, and the like (see FIG. 26) or some inert oil (such as, but not limited to, olive oil, canola oil, cottonseed oil, heavy or light mineral oil, mixtures of the foregoing or subcomponents of the foregoing, or the like). The solvent system is kept in a stirred state. The tiny polymer-drug microspheres are mixed into the solvent, where they remain separate from each other since the aqueous droplets are immiscible with the solvent system. Based on the concentration of the polymer-drug solution being aerosolized, the spray head configuration, and/or possibly other parameters (e.g., pressure applied to the solution, velocity of air or gas passed over the solution, or the like), the size of the microspheres can range from about 0.05-50 micrometers in diameter, more preferably, from about 0.5-5 micrometers in diameter. An emulsifying agent such as Span 85 may or may not be present in the solvent system. The solvent system may be at temperatures ranging from 5 degrees C. to 60 degrees C., depending on the nature of the drug being encapsulated. After all the solution is aerosolized the stirring is continued for a period of ½-2 hours. The microspheres are hardened by surface cross linking by the use of a) glutaraldehyde vapors in a desiccator or by b) immersing the dried microspheres in a solvent system consisting of varying proportions of glutaraldehyde ranging from 0.5-20% w/v of glutaraldehyde in butanol or some similar solvent system. The microspheres are then washed several times with solvents such as, but not limited to, ethanol, methanol or butanol or hexane, depending on the nature of the drug being encapsulated. Removal of water from the spheres leading to a hard surface is achieved either by a) freeze drying the microspheres b) by using a dehydrating agent such as calcium carbonate in a desiccator to remove the water or by c) drying in a vacuum oven at temperatures ranging from about 25-100 degrees C., depending on the nature of the drug. The nebulizer (aerosolizer) used is one that could be of the ultrasonic type (Omron MicroAir, NE-U03V) or any device which produces a fine mist-like spray for example a) even a simple device such as a perfume sprayer could be used, or an air pressurized nozzle type device could be used. Other spray producing devices and mechanisms are known to those of ordinary skill in the art and are not discussed in detail herein.

Some of the advantages of this method are as follows:

a) The particle sizes produced can be from about 0.05-50 micrometers.
b) The particle size distribution of each batch is in a very narrow range.
c) The method is very reproducible.
d) Large batch sizes can be produced in a short time, making this procedure very favorable for large scale production. The process is more akin to a continuous flow process.

Example 6

Bioactive Protein Drug NF-KB

Application-Septic Shock

Method of Preparation-Nebulization

Preparation of Microspheres Containing Cytokine Antagonist Namely Anti-Sense Oligomers to NF-KB (Bio-Active Protein Drug) by the Nebulization Method A) Introduction.

Microspheres containing the cytokine antagonist [(anti-sense oligomer to NF-kB (bio-active protein drug) were evaluated in this study.

B) Preparation of the anti-sense oligonucleotides to NF-kB by albumin using the nebulization method.

Microspheres containing the cytokine antagonist [(anti-sense oligomer to NF-kB (bio-active protein drug)] were cross-linked to the albumin microsphere matrix.

1) 50 mg of human albumin was dissolved in 2 cc of pyrogen free water.
2) The antisense oligonucleotides (oligomers) to NF-kB were separately solubilized in phosphate buffered saline (PBS) at a concentration of 25 mg/cc.
3) The above two solutions were mixed together for approximately 30 minutes.
4) The resulting mixture was cooled to 5 degrees C.
5) 20 cc of solvent as outlined below in "Effect of different oils and solvents" was taken in a 50 cc beaker and cooled to 5 degrees C. and maintained at that temperature in an ice bath.
6) The mixture of albumin and oligonucleotides was nebulized into the solvent and the solvent system is kept in a stirred state for 30 minutes.
7) The solvent system containing the microencapsulated albumin-drug microspheres were evaluated for size with the use of a laser particle sizer until the microspheres were about 1 micron in diameter.
8) The microspheres were cross-linked with 0.5 cc of a 25% w/v solution of glutaraldehyde for 1 hour with constant stirring using a tissue homogenizer at high setting while maintaining the temperature at approximately 5 degrees C. with the aid of an ice bath.
9) The microspheres were washed with three 20 cc washes of butanol or ethanol or methanol or hexane and finally sized while being suspended in the final solvent wash, with the aid of sequential HPLC filters (50, 20, 10, 5, and 1 micron size).
10) The microspheres were freeze dried and stores in a refrigerator until used.

In all cases the microspheres were suspended in pyrogen free water or saline before use. In the nebulization step, the particles created at the spray head were conducted via a tube to the container containing the solvent in step 5) above and the tube tip was maintained below the surface of the solvent so that the nebulized particles were introduced into the solvent solution below the air interface surface so as to minimize loss to the atmosphere.

The above procedure was repeated in order to evaluate to use of different types of oils and solvent systems as the emulsifying media, and different temperatures on manufacture were also evaluated in addition to the 5 degree C. described above. Finally, in addition to water, different solvents were also evaluated as the media for dissolution of the drug. The following variations were evaluated:

a) Effect of Different Oils and Solvents:

Different oils/solvents such as olive oil, cottonseed oil, canola oil, mineral oil and butanol were used for the study.

b) Effect of Different Temperatures:

The microspheres were prepared under wide variations of temperature conditions.

c) Effect of Different Aqueous Phase Used to Dissolve the Drug:

In addition to PBS, saline, distilled/de-ionized water and water with Tween® 80 were used to dissolve the albumin and the drug.

d) Effect of Different Cross-linking Variations:

The effect of cross-linking was evaluated where the cross-linking agent is added after all the microspheres are atomized into the solvent.

C) Experimental Methodology:

a) Drug Content Analysis:

Drug content analysis was determined by HPLC methods developed in our laboratory.

b) Efficacy Studies-In-vitro Whole Blood Model Studies:

The preparations were evaluated for drug efficacy with the aid of the whole blood model, briefly outlined as follows: Blood was pooled into lavender top tubes containing EDTA. The blood was separated into three 5 ml aliquots and pre-treated for 1 hour with one of the following batches of microspheres and challenged with endotoxin (100 mcg/ml). Samples were obtained at 0 and 4 hours post endotoxin challenge to determine the TNF-alpha levels.

D) Results:

FIGS. 1-6 represents the data comparing the Drugs Content and TNF-alpha suppression efficacy of microspheres prepared by the Nebulization Method and the Emulsion Methodology.

Example 7

Chemical Drug Pyrrolidine Dithiocarbamate

Application-Septic Shock

Method of Preparation-Emulsification

Preparation and Evaluation of Microencapsulated

Pyrrolidine Dithiocarbamate

A) Introduction: Pyrrolidine dithiocarbamate (PTDC) is a water soluble, low molecular weight antioxidant substance, which inhibits NF-kB activation. NF-kB is the nuclear transcription factor, which is responsible for the activation of pro-inflammatory cytokines. Several studies have demonstrated the effectiveness of PTDC in cytokine inhibition in-vitro as well as improving mortality in endotoxic shock models in rats. We have demonstrated the improvement of the efficiency of compounds such as neutralizing antibodies and antisense oligomers to NF-kB in cytokine inhibition both in-vitro and in-vivo. Microencapsulation of a compound targets the macrophage and improves the efficiency of cytokine inhibition.

B) Experimental Methodology:

The whole blood model will be used to evaluate the efficacy of the microencapsulated PDTC. Three doses [15 micromoles (uM), 30 uM, and 60 uM] will be studies studied. These doses will be added to 1 ml aliquots in both encapsulated and solution form. TNF alpha will be measured by the standard ELISA procedure.

Figure 27:
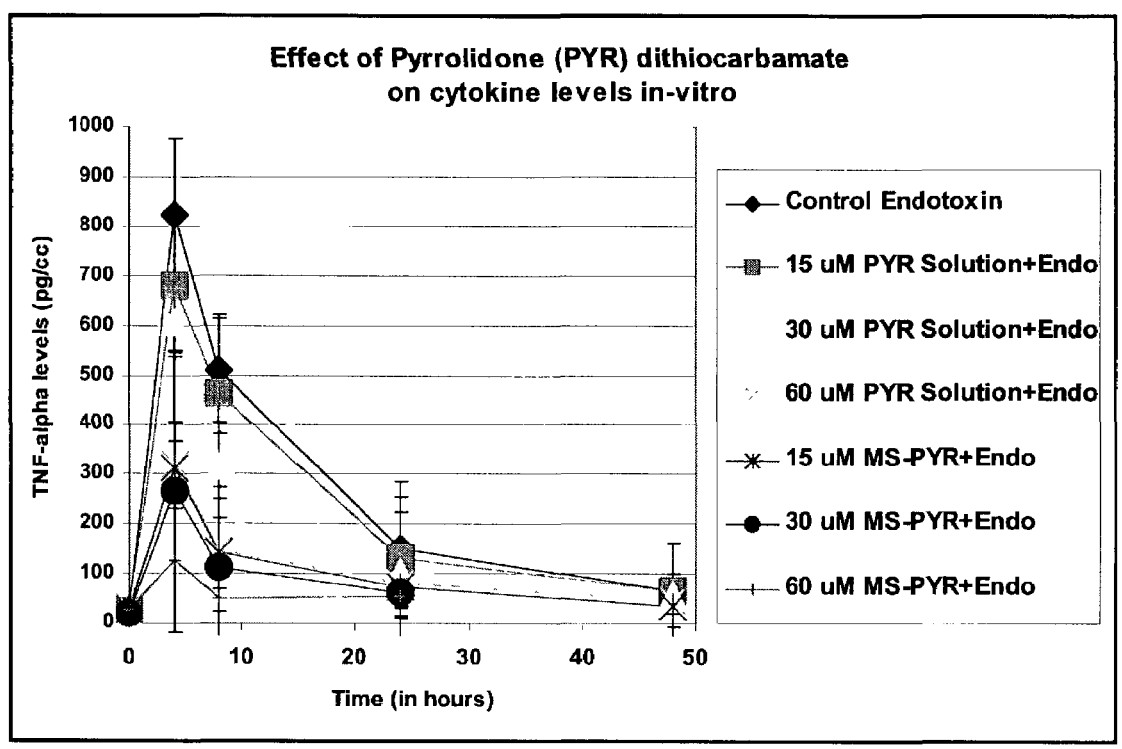
FIG. 27 shows the effect of PDTC on cytokine levels in-vitro.

C) Results:

FIG. 27 shows the effect of PDTC on cytokine levels in-vitro. The microspheres of PDTC were significantly different from the corresponding solution doses at the three doses evaluated.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

The invention claimed is:

1. A method of encapsulating antisense oligonucleotides (oligomers) to NF-kB, comprising the steps of:
    a) dissolving albumin in water;
    b) solubilizing said antisense oligonucleotides (oligomers) to NF-kB in an aqueous phase selected from the group consisting of phosphate buffered saline (PBS), saline, water and water with Tween® 80;
    c) mixing said dissolved albumin and said solubilized antisense oligonucleotides (oligomers) to NF-kB together;
    d) cooling said mixture formed in step c);
    e) cooling a nonaqueous first solvent comprising either a lower carbon alcohol selected from the group consisting of methanol, ethanol, propanol, and butanol or an inert oil selected from the group consisting of olive oil, canola oil, cottonseed oil, mineral oil, mixtures of the foregoing oils and subcomponents of the foregoing oils;
    f) nebulizing the mixture of step d) into said cooled nonaqueous first solvent while said nonaqueous first solvent is stirred so as to form microspheres containing antisense oligonucleotides (oligomers) to NF-kB;
    g) crosslinking said microspheres with glutaraldehyde while stirring;
    h) washing said microspheres of step g) with a second solvent;
    i) sizing said microspheres of step h); and,
    j) freeze drying said microspheres of step i),
    whereby said antisense oligonucleotides (oligomers) to NF-kB are encapsulated in said microspheres.

2. A method for microenencapsulating antisense oligomers to NF-kB, comprising the steps of:
    a) dissolving albumin in water;
    b) solubilizing said antisense oligomers to NF-kB in an aqueous solution selected from the group consisting of phosphate buffered saline (PBS), saline, water and water with Tween® 80;
    c) preparing a mixture by combining the dissolved albumin and the solubilized antisense oligomers to NF-kB;
    d) cooling said mixture of step c);
    e) nebulizing said cooled mixture of step d) into a cooled nonaqueous first solvent comprising either a lower carbon alcohol selected from the group consisting of methanol, ethanol, propanol, and butanol or an inert oil selected from the group consisting of olive oil, canola oil, cottonseed oil, mineral oil, mixtures of the foregoing oils and subcomponents of the foregoing oils while said nonaqueous first solvent is stirred so to form microspheres;
    f) crosslinking said microspheres; and,
    g) washing said crosslinked microspheres.

3. The method as claimed in claim 2, wherein the microspheres are crosslinked with glutaraldehyde.

4. The method as claimed claim 2, wherein the crosslinked microspheres are washed with a second solvent.

5. A method for microenencapsulating a bioactive material, comprising the steps of:
   a) preparing a mixture by combining a dissolved biodegradable polymer and said bioactive material solubilized in an aqueous solution selected from the group consisting of phosphate buffered saline (PBS), saline, water and water with Tween® 80;
   b) cooling said mixture;
   c) nebulizing said mixture of step b) into a cooled nonaqueous first solvent comprising either a lower carbon alcohol selected from the group consisting of methanol, ethanol, propanol, and butanol or an inert oil selected from the group consisting of olive oil, canola oil, cottonseed oil, mineral oil, mixtures of the foregoing oils and subcomponents of the foregoing oils while stirring said nonaqueous first solvent so as to form microspheres;
   d) crosslinking said microspheres; and
   e) washing said crosslinked microspheres with a second solvent.

6. The method as claimed in claim 5, wherein the bioactive material is antisense oligonucleotides (oligomers) to NF-kB.

7. The method as claimed in claim 5, wherein the bioactive material is pyrrolidine dithiocarbamate.

8. The method as claimed in claim 5, wherein the first solvent is an inert oil.

9. The method as claimed in claim 5, wherein the first solvent is an alcohol selected from the group consisting of methanol, ethanol, propanol and butanol.

10. The method as claimed in claim 5, wherein the first solvent is an oil selected from the group consisting of olive oil, cottonseed oil, canola oil, mineral oil and combinations thereof.

11. The method as claimed in claim 5, wherein the bioactive material contains oligonucleotide.

12. The method as claimed in claim 5, wherein the bioactive material is a therapeutic agent.

13. The method as claimed in claim 5, wherein the bioactive material is a drug selected from group consisting of drugs, synthetic drugs, and bioactive proteins.

14. The method as claimed in claim 5, wherein the bioactive material is an aqueous solubolizable drug.

15. The method as claimed in claim 5, wherein the bioactive material is Clodronate.

16. The method as claimed in claim 5, wherein the bioactive material is a guanylhydrazone which can inhibit p38 MAP kinase.

17. The method as claimed in claim 5, wherein the solvent is cooled to a temperature between about 5 and about 40 degrees Celsius.

18. The method as claimed in claim 5, wherein the buffered solution is selected from the group consisting of water and saline.

19. The method as claimed in claim 5, wherein the buffered solution is a phosphate buffered saline.

20. The method as claimed in claim 5, wherein the microspheres are crosslinked by glutaraldehyde.

21. The method as claimed in claim 5, further comprising the step of:
   f) drying the microspheres.

22. The method as claimed in claim 21, wherein the microspheres are dried by freeze drying.

23. The method as claimed in claim 21, wherein the microspheres are dried by heating in a vacuum oven at a temperature between about 25 and about 100 degrees Celsius.

24. The method as claimed in claim 21, wherein the microspheres are dried by using a dehydrating agent.

* * * * *